(12) United States Patent
Wampler

(10) Patent No.: US 8,409,276 B2
(45) Date of Patent: Apr. 2, 2013

(54) HEART ASSIST DEVICE

(76) Inventor: Richard Wampler, Loomis, CA (US)

( * ) Notice: Subject to any disclaimer, the term of this patent is extended or adjusted under 35 U.S.C. 154(b) by 287 days.

(21) Appl. No.: 12/324,430

(22) Filed: Nov. 26, 2008

(65) Prior Publication Data

US 2009/0149950 A1 Jun. 11, 2009

Related U.S. Application Data

(63) Continuation of application No. PCT/US2007/070155, filed on May 31, 2007.

(60) Provisional application No. 60/809,883, filed on May 31, 2006.

(51) Int. Cl.
*A61M 1/12* (2006.01)

(52) U.S. Cl. ............... 623/3.13; 623/3.1; 600/16

(58) Field of Classification Search ......... 623/3.1–3.14; 600/16–17; 417/423.1, 423.7, 423.14, 355, 417/356, 365, 420, 423.12, 423.13; 415/104, 415/107, 110–111
See application file for complete search history.

(56) References Cited

U.S. PATENT DOCUMENTS

| | | | |
|---|---|---|---|
| 4,625,712 A | 12/1986 | Wampler | |
| 4,994,078 A | 2/1991 | Jarvik | |
| 5,092,879 A | 3/1992 | Jarvik | |
| 5,112,200 A | 5/1992 | Isaacson et al. | |
| 5,211,546 A | 5/1993 | Isaacson et al. | |
| 5,370,509 A | 12/1994 | Golding et al. | |
| 5,928,131 A | 7/1999 | Prem | |
| 6,120,537 A * | 9/2000 | Wampler | 623/3.14 |
| 6,293,901 B1 | 9/2001 | Prem | |
| 6,363,276 B1 * | 3/2002 | Prem et al. | 607/6 |
| 6,422,990 B1 | 7/2002 | Prem | |
| 6,530,876 B1 | 3/2003 | Spence | |
| 7,416,525 B2 | 8/2008 | Wampler et al. | |
| 7,431,688 B2 | 10/2008 | Wampler et al. | |

OTHER PUBLICATIONS

Canadian Intellectual Property Office, related patent application No. 2,687,114, office action issued May 24, 2012, with claims examined, pp. 1-22.
Australian Government IP Australia, related application No. 2007266459, office action issued May 15, 2012, with claims examined, pp. 1-4.
European Patent Office, European Supplementary Search Report Issued Oct. 9, 2012, related EPO application No. EP 07797971 (pp. 1-10) including claims searched (pp. 10-13) pp. 1-13.
Wang et al., "Design and Analysis of a Permanent Magnet Motor Integrated with Journal Bearing," Industry Applications Conference, 1997. Thirty-Second IAS Annual Meeting, Conference Record of the 1997 IEEE, New Orleans, LA Oct. 5-7, 1997, vol. 1, Oct. 5, 1997, pp. 24-28 (pp. 1-5).

* cited by examiner

*Primary Examiner* — David Isabella
*Assistant Examiner* — Suba Ganesan
(74) *Attorney, Agent, or Firm* — John P. O'Banion

(57) ABSTRACT

A heart assist device comprising a rotary pump housing having a cylindrical bore, a pumping chamber and a motor stator including an electrically conductive coil located within the housing and surrounding a portion of the cylindrical bore. A rotor has a cylindrical shaft, at least one impeller appended to one end of the shaft, and a plurality of magnets located within the shaft. The rotor shaft is positioned within the housing bore with the magnets opposite the motor stator, and the impeller is positioned within the pumping chamber. The housing bore is closely fitted to the outer surface of the shaft forming a hydrodynamic journal bearing, with the pumping chamber and journal bearing connected by a leak path of blood flow between the pumping chamber and the journal bearing. A backiron of the motor stator attracts the rotor magnets to resist longitudinal displacement of the rotor within the housing during operation. The relative orientation of positions of the inflow, outflow, and leakage flow paths may be varied within the pump, such as to accommodate different intended methods for implantation and/or use.

15 Claims, 14 Drawing Sheets

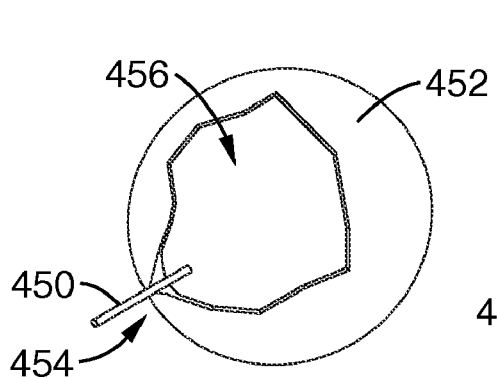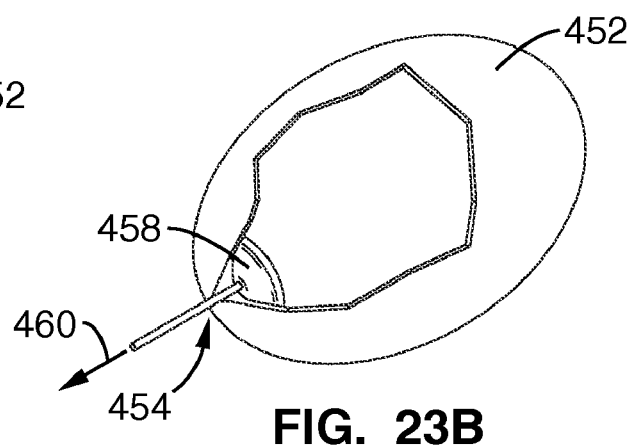
FIG. 23A    FIG. 23B
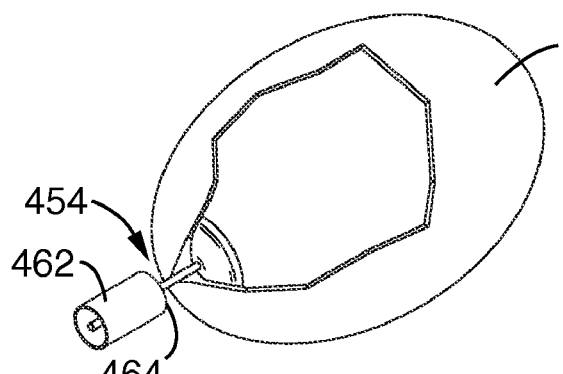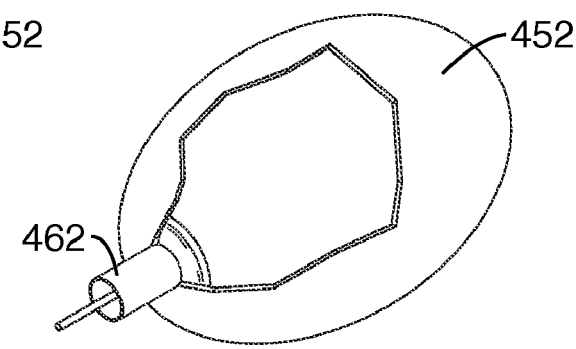
FIG. 23C    FIG. 23D
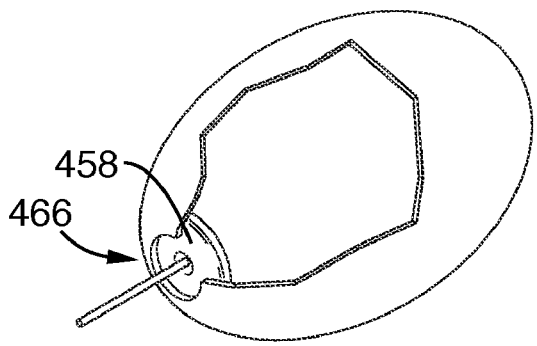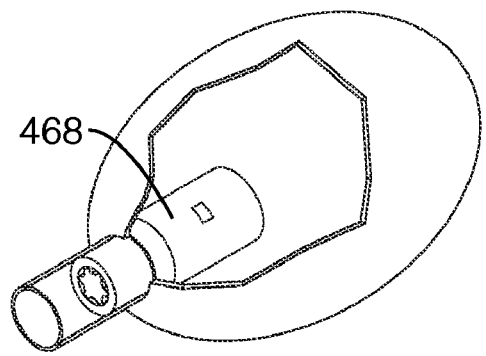
FIG. 23E    FIG. 23F

HEART ASSIST DEVICE

CROSS-REFERENCE TO RELATED APPLICATIONS

This application claims priority from, and is a 35 U.S.C. §111(a) continuation of, co-pending PCT international application serial number PCT/US2007/070155, filed on May 31, 2007, incorporated herein by reference in its entirety, which claims priority from U.S. provisional application Ser. No. 60/809,883, filed on May 31, 2006, incorporated herein by reference in its entirety.

STATEMENT REGARDING FEDERALLY SPONSORED RESEARCH OR DEVELOPMENT

Not Applicable

INCORPORATION-BY-REFERENCE OF MATERIAL SUBMITTED ON A COMPACT DISC

Not Applicable

NOTICE OF MATERIAL SUBJECT TO COPYRIGHT PROTECTION

A portion of the material in this patent document is subject to copyright protection under the copyright laws of the United States and of other countries. The owner of the copyright rights has no objection to the facsimile reproduction by anyone of the patent document or the patent disclosure, as it appears in the United States Patent and Trademark Office publicly available file or records, but otherwise reserves all copyright rights whatsoever. The copyright owner does not hereby waive any of its rights to have this patent document maintained in secrecy, including without limitation its rights pursuant to 37 C.F.R. §1.14.

BACKGROUND OF THE INVENTION

1. Field of the Invention

This invention pertains generally to methods and devices for assisting the flow of blood through the heart.

2. Description of Related Art

Congestive heart failure is a major global public health problem that results in hundreds of thousands of deaths and incalculable human suffering in millions of people each year. Current treatments included modern pharmacologic agents, automatic internal defibrillators and advanced pacing devices including synchronizers. These modalities offer some symptomatic improvement and, potentially, improve survival but all are palliative treatments at best and are not curative.

Existing therapies provide limited clinical benefits for patients in advanced stages of congestive heart failure. In fact, it is estimated that several hundred thousand patients each year with far advanced CHF experience only limited clinical benefit from existing well-established treatments, and could best be served by cardiac transplantation. Cardiac transplantation offers significant improvement in symptoms and survival for patients with end stage heart failure but is available to only a few thousand patients each year due to the limited number of donor hearts.

Mechanical circulatory assistance (MCA), in the form of a total artificial heart (TAH) or a left ventricular assist device (LVAD), has the potential to meet the needs of these patients with end stage heart failure for whom there is little hope. Unfortunately, mechanical circulatory assistance has not developed into a commonly used therapy in the treatment of heart failure.

Historically, there has been substantial evolution in the technology of mechanical circulatory assistance and changes in the paradigms regarding the efficacy of MCA and its role in the treatment of heart failure. The original paradigm envisioned the development of a mass-produced pulsatile TAH that could be implanted routinely in many hundreds of thousands of end stage patients who could otherwise benefit from cardiac transplantation. However, technical challenges have, thus far, precluded the development of the practical TAH needed to achieve the original vision.

Subsequently, it was proposed that LVADs could address the needs of most end stage patients and numerous LVADs have been developed in the last thirty years. Indeed, a number of effective LVADs have shown promise in clinical studies but have experienced only limited commercial success. Such devices include both pulsatile and rotary continuous flow pumps.

Clinical research has shown that LVADs have powerful hemodynamic effectiveness and offer substantial clinical benefit as bridges to cardiac transplantation and in treating post-cardiotomy shock. Recent experience with LVADs for destination therapy in patients who could benefit but are not candidates for cardiac transplantation, has demonstrated improvement in symptoms, quality of life and survival. Serendipitously, significant spontaneous recovery in left ventricular function has been observed in some bridge patients awaiting donor hearts. In some patients who experience spontaneous recovery of left ventricular function it has been possible to remove the assist device and delay or avoid the need for cardiac transplantation.

The phenomenon of spontaneous ventricular recovery in mechanically assisted patients who were thought to have a progressive irreversible pathology suggests some exciting possibilities. If significant left ventricular recovery can occur in patients with far advanced heart failure, perhaps the use of mechanical circulatory assistance in patients with less advanced disease could arrest or reverse the fundamental pathology of CHF in large numbers of patients. If such were the case, a radical paradigm shift in the treatment of congestive heart failure and the perceived role of left ventricular assist devices could take place. If a significant number of patients with CHF have the potential for reversing pathology, then the primary goal of the treatment of CHF could shift from the palliative treatment of symptoms to the treatment of the underlying progressive pathology in order to reverse the primary ventricular pathology. Ventricular assist devices could emerge as true therapeutic modalities rather than bridges to cardiac transplantation and palliation for end stage patients. Such a paradigm shift will require the development of ventricular assist device systems that requires much less invasive procedures for insertion than existing ones; specifically, systems that do not require a cardiac surgeon or cardiopulmonary bypass.

Intravascular transvalvular ventricular assistance has been used on a limited basis in patients and has demonstrated significant clinical benefit in the setting of acute cardiogenic shock, failure to wean from cardiopulmonary bypass, assisted high risk angioplasty and, beating heart coronary revascularization. More specifically, two non-thoracotomy methods for achieving central vascular access have been previously described and have been used to a limited extent in patients. These methods are transeptal cannulation of the left atrium and transvalvular cannulation of the left ventricle.

One previous disclosure alleges a method for cannulating the left atrium without a thoracotomy for total cardiopulmonary bypass. This method included placing a 7 mm cannula via the jugular vein through the atrial septum into the left atrium and placing a similar cannula into a peripheral artery. A pump was then placed between the two cannulae such that it withdrew oxygenated blood from the left atria and pumped it into the arterial system. This approach has been used to a limited extent to treat patients with acute cardiogenic shock, but has not been adapted for ambulatory or chronic use. Another disclosure has proposed a method for partial ventricular assistance which combines transeptal atrial cannulation with an implantable pump that could, potentially, provide long-term ambulatory ventricular assistance.

Still another prior disclosure proposed a novel non-thoracotomy method for cannulating the left ventricle to implement prolonged ventricular assistance. This method required placing a 5 mm cannula via the carotid artery retrograde across the aortic valve into the left ventricle. The aortic valve leaflets provided a seal against leakage of blood around the inlet cannula. A similar cannula was inserted into a peripheral artery. A pump was then placed between the two cannulae such that it withdrew oxygenated blood from the left ventricle and pumped it into the arterial system. It has been proposed that the subclavian artery in the human could be used for insertion of the transvalvular cannula and the pump outlet connected to the subclavian or femoral artery. Subsequently disclosed embodiments of this approach employed external roller pumps or rotary pumps. However, these embodiments are not generally considered practical for ambulatory or chronic clinical use.

One previously disclosed LVAD system was intended to adapt peripheral transvalvular cannulation of the left ventricle to a miniature (6.5 mm) intravascular blood pump (Hemopump®). This method required insertion of a high-capacity axial flow blood pump into the femoral artery. A flexible inflow cannula attached to the pump was guided retrograde across the aortic valve into the left ventricle. The outlet of the pump was located in the thoracic aorta. Blood was withdrawn from the left ventricle and pumped into the aorta. Power was supplied to the pump via a percutaneous flexible driveable which was driven by an external motor. Another LVAD pump developed by a company called "Impella" is believed to employ a similar method of vascular access but drives the pump with a miniature motor integral with the pump. Electrical power is supplied to the motor via a percutaneous wire.

Both of these LVAD systems noted immediately above are believed to maintain seal integrity with respective external fluid purge systems, but which are further believed to exhibit very limited durability. Neither system has been adapted to ambulatory or chronic use. It is believed that the period of use of these pumps has been limited to about two weeks.

Mechanical circulatory assistance has been shown to be an effective treatment for patients suffering from severe congestive heart failure (CHF). Both left ventricular assist devices (LVADs) and right ventricular assist devices have been adapted for bridging patients to heart transplantation and for long-term (destination) therapy. Unfortunately, existing methods for inserting these devices require major surgery during which the patient is placed on cardiopulmonary bypass and the heart may be arrested while vascular grafts are connected to a chamber of the heart to provide blood inflow to the pump of the assist system.

The implantation of existing LVADs carries too much risk to justify their customary use except in the most extreme circumstances. Current LVADs require a cardiovascular surgeon and cardiopulmonary bypass for implantation. Many previously disclosed devices and prior efforts require that both the abdominal cavity and the thoracic cavity be opened to implant the pump. Subdiaphragmatic placement of the pump necessitates diaphragmatic penetrations, which is desirable to avoid if possible.

Accordingly, left ventricular assist devices have previously been used only rarely in the treatment of CHF and then as a treatment of last resort. This is highly unfortunate, because LVADs offer greater hemodynamic efficacy than virtually all other adapted treatments, and also offer the potential of much greater clinical benefit in the treatment of congestive heart failure than other therapies and comparable to cardiac transplantation.

The substantial risk associated with present methods of implanting LVADs and RVAD has limited their use to end-stage patients. A much larger group of patients with less severe heart disease are not, presently, considered candidates for treatment with mechanical circulatory assist devices because of the substantial risk of implanting circulatory assist devices.

Thus, there remains a need for improved devices and methods that would permit less invasive cannulation of the chambers of the heart without the need for large incisions, cardiopulmonary bypass and the need to arrest the heart. This would make it possible to better serve large numbers of patients with less severe CHF.

The various aspects, modes, embodiments, and features of the present invention, as herein described, variously address certain existing needs such as just described, as well as others, in addition to overcoming and improving upon other shortcomings and deficiencies observed in prior efforts and previously disclosed devices.

BRIEF SUMMARY OF THE INVENTION

The present invention, according to certain aspects, provides methods and devices for minimally and less invasive implantation of mechanical circulatory assist devices. Such a device could find widespread use in the treatment of congestive heart failure, as it can be inserted with minimally or less invasive techniques and be used as an ambulatory chronic ventricular assist device. Use of lower risk minimally or less invasive techniques would make therapeutic ventricular assistance available to class III as well as class IV congestive heart failure patients.

To overcome the barriers and shortcomings incumbent with prior efforts, various aspects of the present invention provide new, improved LVADs and the means for their insertion to lower the risk of their use for the treatment of congestive heart failure. These presently disclosed LVADs provide improved safety and simplicity to place in the patient, in particular with minimally and less invasive methods of insertion. According to certain embodiments, LVADs are disclosed which are adapted to be used in the treatment of congestive heart failure by the interventional cardiologist without the need for cardiac surgical support and without the need for a thoracotomy. It is believed that appropriate implementation of the presently disclosed embodiments may become the standard of care in many circumstances. The devices according to further embodiments can be inserted in much the same fashion as the implantable defibrillator, while in certain circumstances perhaps to be supplemented with the aid of a vascular surgeon.

One aspect of the present invention accordingly provides a device comprising a rotary pump housing having a cylindrical bore, a pumping chamber and a motor stator including an electrically conductive coil located within the housing and surrounding a portion of the cylindrical bore, and also comprising a rotor, the rotor having a cylindrical shaft and at least one impeller appended to or otherwise located along one end of the shaft. The rotor comprises a plurality of magnets located within the shaft and opposite the motor stator, the bore is closely fitted to the outer surface of the shaft forming a hydrodynamic journal bearing, and the at least one impeller of the rotor is positioned within the pumping chamber. The pumping chamber and the journal bearing are connected by a leak path to allow blood to pass from the pumping chamber into the journal bearing.

In one mode of this aspect, passage of blood into the pumping chamber is provided by inlets provided in the pump housing formed between the pumping chamber and the cylindrical bore. In another mode, the shaft is hollow and forms an inlet for passage of blood into the pumping chamber. In another mode, an inlet for passage of blood is provided through at least one channel formed longitudinally in the cylindrical bore of the housing.

In another mode, the shaft flares at an end longitudinally opposed to the impeller thereby forming a radial projection over at least a portion of the bore of the housing. The projection forms a hydrodynamic thrust bearing at the bore end portion for opposing axial thrusting of the rotor.

In another mode, the rotor is suspended within the housing by hydrodynamic thrust forces generated by relative movement of the impeller with respect to and within the pumping chamber.

In another mode, the impeller and the shaft are integral.

In another mode, the pumping action has a nominal flow of at least about five liters per minute. In one embodiment, the pumping action has a nominal flow of at least about six liters per minute.

In another mode, the pump housing has a diameter of about 1.25 inches or less. In one embodiment, the pump housing has a diameter of about 1.0 inches or less. In a further embodiment, the pump housing has a diameter of about 0.9 inches or less.

In another mode, the pump housing has a length of about 1.75 inches or less. In one embodiment, the pump housing has a length of about 1.50 inches or less. In a further embodiment, the pump housing has a length of about 1.30 inches or less.

In another mode, the pump housing has a weight of about 75 grams or less. In one embodiment, the pump housing has a weight of about 60 grams or less, while in a further embodiment, the pump housing has a weight of about 50 grams or less.

The pump according to another mode permits the displacement of at least about 15 cc. In one embodiment, the pump displaces at least about 17 cc. In another embodiment, the pump displaces at least about 20 cc.

According to another mode, the pump is adapted to be coupled to an energy source.

According to another mode, power consumption for the pump is preferably about 5 watts or less at 100 mm Hg.

Another aspect of the present invention is a method for surgically implanting a heart assist device comprising, a) exposing a heart to provide access of the intended heart chamber and allow facilitated insertion of an inflow cannula into the heart; b) inserting an expandable traction device into the chamber of the heart; c) deploying the expandable device and applying traction means to the expanded device such that force is exerted against the interior wall of the heart chamber to exert controlled traction on the wall of the heart chamber to gain control of the intended site for cannulation; d) passing a wire guide into the heart chamber; e) employing a progressive dilation system to enlarge the penetration at the site of incision sufficient to allow introduction of a thin walled sheath; f) inserting a conduit for an inflow cannula or pump into the heart chamber; and g) means for stabilizing the cannula or pump to the chamber wall.

According to one mode of this aspect, after step e) of this method, a sheath is inserted and the inflow cannula or pump is passed through or around the insertion sheath into the heart chamber.

In one embodiment of this mode, the insertion sheath is removable once the inflow cannula or pump is positioned in the heart chamber. In a still another embodiment, the insertion sheath is splittable into segments.

According to another mode of the present aspect, the method further includes use of a stabilizing means. In one embodiment, the stabilizing means comprises a polymeric or elastomeric washer. In a further embodiment, the polymeric or elastomeric washer is secured surgically, such as by suturing, stabling or bonding according to certain more specific exemplary embodiments.

In another mode of the present aspect, the surgical method further utilizes a fast-curing tissue adhesive to attach a circular ring around the site of incision. According to certain further embodiments, the circular ring may be felt, polymeric material or other suitable implantable materials.

In another mode of the surgical method, the traction means comprises a tether or a catheter attached to the expanded device. In one embodiment of this method, after step a) an introducer sheath is inserted to permit the expandable device in step b) to be passed into the chamber of the heart.

According to another mode of the present surgical method, the guide wire is further passed through a valve. In one highly beneficial embodiment, this is performed using the Seldinger technique to pass the guide wire.

In a still further mode of the present surgical method aspect of the invention, the traction means is applied to the wall of the heart using a vacuum. In one such method embodiment, the vacuum employs small suction cups connected to an external vacuum source, where once suction is achieved, mechanical traction is utilized to control the insertion site. In a further embodiment, mechanical traction is applied by a surgical method, such as by use of suture tethers and mechanical rods.

Another aspect of the present invention is an implantable blood pump device that includes a housing and rotor as follows. The housing has an elongated cylindrical bore extending along a longitudinal axis and also with a pumping chamber. The rotor has an elongated shaft extending along a longitudinal axis and with a rotary pump coupled to the elongated shaft. A blood inlet port is fluidly coupled to the pumping chamber. A blood outlet port is fluidly coupled to the pumping chamber. A motor is provided that is configured to be coupled to a power source and to torque the rotor when activated by the power source. The elongated shaft of the rotor is located at least in part within the cylindrical bore of the housing with a journal bearing clearance between an inner bearing surface of the housing's bore and an outer bearing surface of the rotor shaft. The rotary pump is located within the pumping chamber. In an operating mode for the pump, the motor is activated and torques the rotor such that the rotor shaft and rotary pump rotate within the journal bearing clearance and pumping chamber, respectively. Also in the operating mode, fluid enters the pump along an inflow path inward through the inlet port and into the pumping chamber, and is pumped out from the pump principally along an outflow path outward from the pumping chamber through the outlet port, and also flows within the pump along a leakage flow path between the pumping chamber and the journal bearing clearance between the rotor shaft and the housing bore. The leakage flow through the journal bearing clearance forms a hydrodynamic journal bearing between the rotor and housing.

Another aspect is an implantable blood pump with a housing and interfacing rotor as follows. The housing has an elongated cylindrical bore extending along a longitudinal axis, a pumping chamber, and a motor stator. The rotor includes an elongated shaft extending along a longitudinal axis, a rotary pump coupled to the elongated shaft, and a rotor magnet. A blood inlet and outlet ports are fluidly coupled to the pumping chamber. The elongated shaft of the rotor is located at least in part within the cylindrical bore of the housing with a journal bearing clearance between an inner bearing surface of the housing's bore and an outer bearing surface of the rotor shaft. The rotary pump is located within the pumping chamber. The motor stator includes an electrically conductive coil that is adapted to be coupled to a power source and is positioned relative to the rotor magnet to form a flux gap motor interface. In an operating mode, the motor is activated by the power source such that electrical current flow through the coil creates a magnetic flux field that extends across a flux gap clearance between the rotor and housing at the flux gap motor interface. This magnetic flux field displaces the rotor magnet sufficient to torque the rotor and rotate the rotor shaft and rotary pump within the journal bearing clearance and pumping chamber, respectively. Further to this operating mode, fluid flows into the pump principally along an inflow path inward through the inlet port and into the pumping chamber, and is pumped out from the pump principally along an outflow path outward from the pumping chamber through the outlet port. Fluid also flows along a leakage flow path between the pumping chamber and the flux gap clearance between the rotor and housing at the flux gap motor interface to form a hydrodynamic journal bearing at that location.

Another aspect is an implantable blood pump device with a housing and rotor assembly as follows. The housing includes an elongated cylindrical bore extending along a longitudinal axis, a pumping chamber, and a motor stator with an electrically conductive coil and back iron. The rotor includes an elongated shaft extending along a longitudinal axis, a rotary pump coupled to the elongated shaft, and a rotor magnet. Blood inlet and outlet ports are fluidly coupled to the pumping chamber. The elongated shaft of the rotor is located at least in part within the cylindrical bore of the housing with a journal bearing clearance between an inner bearing surface of the housing's bore and an outer bearing surface of the rotor shaft. The rotary pump is located within the pumping chamber. The motor stator is adapted to be coupled to a power source and is positioned relative to the rotor magnet to form a flux gap motor interface in an operating mode upon activation by the power source. In such operating mode, electrical current flows through the coil sufficient to create a magnetic flux field that extends across a flux gap clearance between the rotor and housing at the flux gap motor interface. This magnetic flux field displaces the rotor magnet sufficient to torque the rotor and rotate the rotor shaft and rotary pump within the journal bearing clearance and pumping chamber, respectively. Further to this operating mode, fluid flows into the pump principally along an inflow path inward through the inlet port and into the pumping chamber, and is pumped out from the pump principally along an outflow path outward from the pumping chamber through the outlet port. In the operating mode, the back iron is positioned to provide a magnetic flux field interaction between the back iron and rotor magnet sufficient to substantially resist longitudinal displacement from a displacement force of the activated motor stator coil, and to substantially maintain a longitudinal position of the rotor within the housing.

Another aspect of the present invention is an implantable blood pump with a pump housing, an actuator, and a pump as follows. The pump housing includes an actuator housing and a pumping chamber. The pump is located within the pumping chamber. The actuator is located within the actuator housing and is coupled to the pump. A motor is coupled to the actuator and configured to be coupled to a power source that operates the motor in an operating mode that actuates the actuator to move. In the operating mode, the actuator motion actuates the pump to pump fluid such that fluid flows along a primary inflow path through an inlet port into the pumping chamber, and is pumped along a primary outflow path through an outlet port from the pumping chamber, and also flows along a leakage flow path that includes a hydrodynamic bearing clearance between a moving surface of the actuator relative to the actuator housing.

Another aspect of the present disclosure is an inventive method for configuring and operating an implantable blood pump. This includes providing a rotary pump housing having a cylindrical bore, a pumping chamber and a motor stator including an electrically conductive coil located within said housing and surrounding a portion of said cylindrical bore. The method also includes providing a rotor with a cylindrical shaft with an outer surface and at least one impeller appended to one end of said shaft, and with a plurality of magnets located within said shaft, in addition to: locating the rotor within the housing such that the rotor magnets are opposite said motor stator, with the bore closely fitted to the outer surface of said shaft forming a journal bearing, and locating the impeller within the pumping chamber. The pump actuated into an operating mode that includes rotating the rotor within the bore while rotating the impeller within the pumping chamber. In the operating mode, fluid is allowed to flow along a leakage flow path between the pumping chamber and the journal bearing to thereby form a hydrodynamic journal bearing.

Another aspect of the present disclosure is another inventive method for configuring and operating an implantable blood pump as follows. This method includes providing a blood pump with a housing with an elongated cylindrical bore extending along a longitudinal axis and also with a pumping chamber. It also includes providing a rotor with an elongated shaft extending along a longitudinal axis and with a rotary pump coupled to the elongated shaft, and positioning the rotor within the housing such that: the rotor shaft is located within the cylindrical bore with a journal bearing clearance between an inner bearing surface of the housing's bore and an outer bearing surface of the rotor shaft, and the rotary pump is located within the pumping chamber. A motor is also provided and is configured for coupling to a power source and for torquing the rotor when the motor is activated by the power source. The pump is configured into an operating mode by activating the motor and torquing the rotor with the motor such that the rotor shaft and rotary pump rotate within the journal bearing clearance and pumping chamber, respectively. In the operating mode, fluid is allowed to enter the pump along an inflow path inward through an inlet port and into the pumping chamber, is pumped out from the pump principally along an outflow path outward from the pumping chamber through an outlet port, and is also allowed to flow along a leakage flow path between the pumping chamber and the journal bearing clearance between the rotor shaft and the housing bore. Further to the operating mode, a hydrodynamic journal bearing is provided between the rotor and housing via the leakage flow through the journal bearing clearance.

Another aspect of the present disclosure is another inventive method for configuring and operating an implantable blood pump as follows. A pump is provided with a housing with an elongated cylindrical bore extending along a longitudinal axis, a pumping chamber, and a motor stator. A rotor is provided with an elongated shaft extending along a longitudinal axis, a rotary pump coupled to the elongated shaft, and a rotor magnet. The elongated shaft of the rotor is positioned at least in part within the cylindrical bore of the housing with a journal bearing clearance between an inner bearing surface of the housing's bore and an outer bearing surface of the rotor shaft. The rotary pump is positioned within the pumping chamber. The motor stator is configured with an electrically conductive coil that is adapted to be coupled to a power source and that is positioned relative to the rotor magnet to form a flux gap motor interface. The pump is configured in an operating mode by activating the motor stator with the power source such that electrical current flows through the coil and creates a magnetic flux field that extends across a flux gap clearance between the rotor and housing at the flux gap motor interface. This displaces the rotor magnet with the magnetic flux field sufficient to torque the rotor, and rotating the rotor shaft and rotary pump within the journal bearing clearance and pumping chamber, respectively. Also in the operating mode, fluid flows into the pump principally along an inflow path inward through an inlet port and into the pumping chamber, and is pumped out from the pump principally along an outflow path outward from the pumping chamber through an outlet port. Fluid also flows along a leakage flow path that includes the flux gap clearance between the rotor and housing at the flux gap motor interface to thereby form a hydrodynamic journal bearing.

Another aspect of the present disclosure is another inventive method for configuring and operating an implantable blood pump as follows. A blood pump is provided with a housing with an elongated cylindrical bore extending along a longitudinal axis, a pumping chamber, and a motor stator with an electrically conductive coil and back iron. A rotor is provided with an elongated shaft extending along a longitudinal axis, a rotary pump coupled to the elongated shaft, and a rotor magnet. The elongated shaft of the rotor is positioned at least in part within the cylindrical bore of the housing with a journal bearing clearance between an inner bearing surface of the housing's bore and an outer bearing surface of the rotor shaft. The rotary pump is positioned within the pumping chamber. The motor stator is configured for coupling to a power source and in a position relative to the rotor magnet to form a flux gap motor interface when activated. The pump is configured into an operating mode by activating the motor stator with the power source, allowing electrical current to flow through the coil sufficient to create a magnetic flux field that extends across a flux gap clearance between the rotor and housing at the flux gap motor interface. This displaces the rotor magnet under force of the magnetic flux field sufficient to torque the rotor and rotate the rotor shaft and rotary pump within the journal bearing clearance and pumping chamber, respectively. In the operating mode, fluid flows into the pump principally along an inflow path inward through an inlet port and into the pumping chamber, and is pumped out from the pump principally along an outflow path outward from the pumping chamber through an outlet port. Also in the operating mode, the back iron is positioned so as to provide a magnetic flux field interaction between the back iron and rotor magnet sufficient to substantially resist longitudinal displacement from a displacement force placed upon the rotor upon activation of the motor stator. This arrangement thereby substantially maintains a longitudinal position of the rotor within the housing during operation.

Another aspect of the present disclosure provides another inventive method for configuring and operating an implantable blood pump, as follows. A blood pump is provided with a housing with an actuator housing and a pumping chamber. A pump is positioned within the pumping chamber. An actuator is positioned within the actuator housing. The actuator is coupled to the pump within the housing. A motor is coupled to the actuator and is configured for coupling to a power source that activates the motor in an operating mode. In the operating mode, the actuator is moved by the activated motor, and the pump is actuated by the actuator's motion to pump fluid through the pumping chamber. In this operating mode, fluid flows along a primary inflow path through an inlet port into the pumping chamber, and is pumped along a primary outflow path through an outlet port from the pumping chamber. Fluid also flows along a leakage flow path between the pumping chamber and a hydrodynamic bearing clearance between a moving surface of the actuator relative to the actuator housing.

According to one mode of the various aspects herein described, a leakage flow path provided by a particular pump aspect may further flow through, across, or include a flux gap interface between a flux gap motor stator coupled to a cylindrical bore portion of the housing and a rotor magnet coupled to a rotor shaft region that is mechanically coupled to an impeller pump within the pumping chamber. According to one embodiment, the motor stator is located along the cylindrical bore of the housing, the rotor magnet is located along a rotor shaft section, and the magnetic flux gap extends across the journal bearing clearance between the rotor shaft and cylindrical bore of the housing. According to one further embodiment, the inflow path into the inlet port is axially aligned along the longitudinal axis of rotation of the rotor and is forward of the pumping chamber, the outlet ports are radially displaced along the housing transverse to the longitudinal axis, the rotor is located rearward of the pumping chamber, and the leakage flow path extends from the pumping chamber and along the journal bearing clearance between the rotor shaft and the cylindrical housing bore.

According to another mode of the various aspects of blood pumps and their uses presented hereunder, the fluid flowing through the pump comprises a priming fluid run through the pump externally of the patient in order to purge the pump of air and prepare the pump for implantation. In one embodiment, such priming fluid comprises a saline solution; in another it comprises a lactated ringer's solution.

According to another mode, the fluid flowing through the pump comprises blood, which may be either as a primed pump or as implanted within the patient.

According to another mode, leakage flow is boosted through the pump using a hydrodynamic thrust bearing pump fluidly coupled to the leakage flow path, such as in particular coupled to a hydrodynamic journal bearing between a rotor shaft and cylindrical bore of the pump housing.

According to still a further mode, the systems, devices, and methods further involve implanting the pump within a patient's body with blood inflow and blood outflow of the pump coupled to the patient's vascular system. More specific modes, embodiments, and features of this will become clear by a further reading of this disclosure, and constitute still further inventive aspects considered of particular further benefit to those specifically noted above.

These and other features and advantages of this invention are described in, or are apparent from, the following detailed description of various exemplary embodiments of the devices and methods according to this invention without placing limitations thereon.

BRIEF DESCRIPTION OF THE SEVERAL VIEWS OF THE DRAWING(S)

The invention will be more fully understood by reference to the following drawings which are for illustrative purposes only:

FIGS. 1A-B show a schematic view of an anatomical placement of a minimally invasive intravascular transvalvular ventricular assist device.

FIGS. 2A-B show a schematic view of an anatomical placement of a minimally invasive ventricular assist system with an intravascular transvalvular inflow cannula and a subcutaneous pump.

FIGS. 3A-B show a schematic view of an anatomical placement of a less invasive ventricular assist system with an intraventricular pump and transvalvular outflow.

Figure 1A:
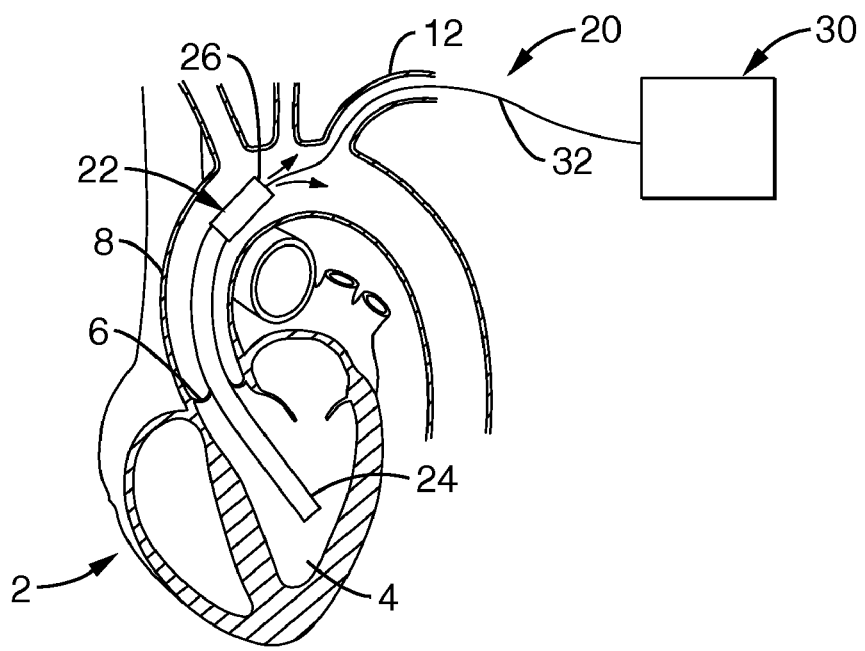

FIGS. 23A-F show schematic views of sequential steps of using one delivery system of cooperating component devices according to one particular method for transapical surgical implantation of a blood pump of the present disclosure within a left ventricle in a patient.

DETAILED DESCRIPTION OF THE INVENTION

Referring more specifically to the drawings, for illustrative purposes the present invention is embodied in the apparatus generally shown in FIG. 1A through FIG. 23F. It will be appreciated that the apparatus may vary as to configuration and as to details of the parts, and that the method may vary as to the specific steps and sequence, without departing from the basic concepts as disclosed herein.

It is to be appreciated that significantly beneficial objectives of minimally invasive and less invasive insertion methods are permitted by various of the device embodiments of the present invention, as herein described and apparent to one of ordinary skill based upon a comprehensive review of the present disclosure. Two particularly beneficial methods for less invasive surgical implantation are disclosed, though without limitation, and which include: 1) insertion without vascular anastomosis, and 2) insertion with vascular anastomosis.

Minimally invasive insertion is considered of particular benefit to the extent that it allows the implementation of LVADs without a thoracotomy or cardiopulmonary bypass. Central vascular access is considered of particular benefit to the extent that it is achieved via peripheral vascular access, such as for example using fluoroscopic guidance, for the placement of either an intravascular pump or specialized cannulas.

Less invasive insertion is considered of particular benefit to the extent that it includes placing the LVAD with a limited surgical incision and without cardiopulmonary bypass. Methods which eliminate the need for vascular anastomoses are furthermore considered very advantageous, and are beneficially achieved according to certain of the present embodiments. Adaptation to an insertion method facilitated by thorascopic techniques further simplifies the procedure, and is also achieved by certain of the present embodiments.

Minimally invasive placement of LVADS is generally considered to fall, predominately, within the domain of the interventional cardiologist (though clearly other adequately trained and capable physicians may practice the present invention). Adaptation for use by such interventionalist is provided by certain of the present embodiments, in particular in that such devices generally allow at least one of, and preferably more than one or all of: 1) a simple means for achieving non-thoracotomy vascular access, 2) small cannula systems and miniature pumps suitable for insertion in peripheral arteries, 3) small pumps suitable for subcutaneous implantation on the chest wall, and 4) pumps capable of operating reliably for months to years in an ambulatory setting. An ability to provide minimally or less invasive implantation of LVADs capable of operating reliably in extended ambulatory is a particular benefit presented by certain of the present embodiments and not previously possible by devices and methods of prior disclosures or use.

Various methods are made available by certain present embodiments and which are based on transvascular techniques familiar to the interventional cardiologist. Such methods typically employ placement of a flexible cannula retrograde across the aortic valve to serve as an inflow conduit to a pump. Non-thoracotomy placement of the inflow cannula will typically be via peripheral arterial access. One illustrative method employs placement of a miniature intravascular pump which receives power from an external controller and battery via a percutaneous wire.

For further illustration of one particular method, FIG. 1A shows a pump system 20 that includes a pump 22 that is miniaturized and is placed within an artery of an arterial system. An inflow cannula 24 is placed retrograde across an aortic valve 6 into left ventricle 4 of heart 2. The pump outlet 26 is positioned in an ascending aorta 8 of the arterial system. Blood is removed from the left ventricle 4 via the inflow cannula 24 and pumped into the ascending aorta 8 via outlet 26, thus, directly assisting the left ventricle 4.

Figure 1B:
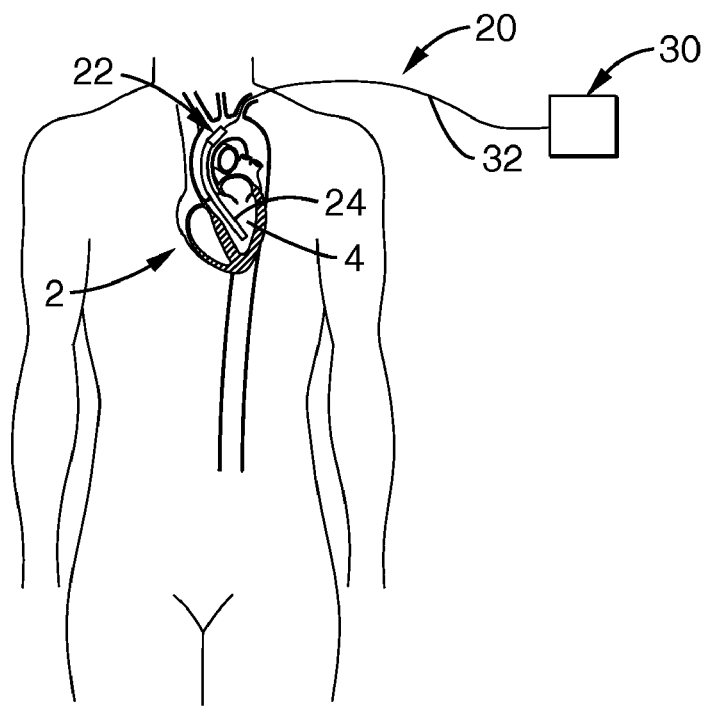

As shown schematically in FIG. 1B, power is supplied to the pump 20 via a percutaneous wire 32 from an externally worn motor controller and rechargeable battery system 30. In the particular illustration shown, wire 32 is coupled from the external system components to the pump via subclavian artery 12.

As will be appreciated by one of ordinary skill, certain of the particular pump embodiments elsewhere herein shown and described in further detail are readily adapted for use in accordance with this presently illustrated method and configuration between component parts. This is particularly the case, for example, with respect to the embodiment illustrated in FIG. 18 and FIG. 19.

Figure 2A:
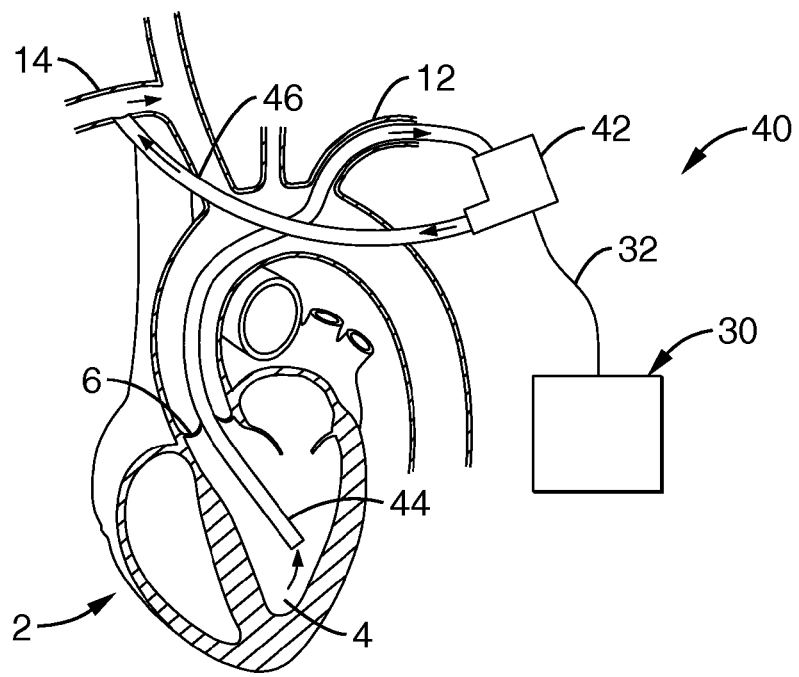
Figure 2B:
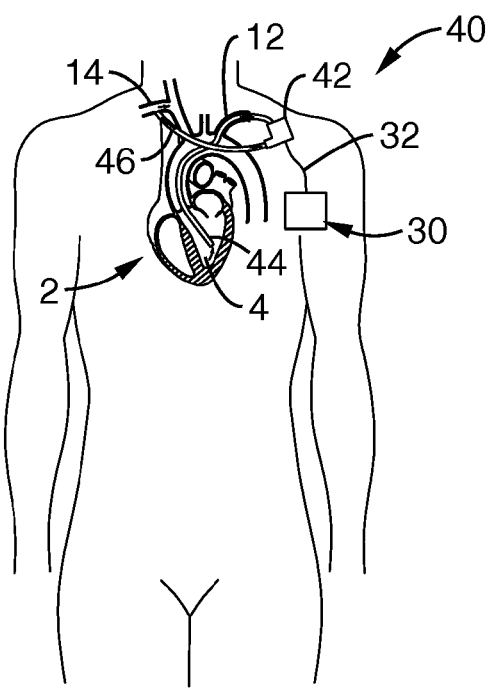

FIG. 2A shows the anatomical placement of a system 40 in which a pump 42 is located in a subcutaneous pouch in a pectoral region of a patient. The inflow of the pump 42 is in continuity with a flexible inflow cannula 44 which enters the subclavian artery 12 and traverses retrograde across the aortic valve 6 into the left ventricle 4. A second outflow cannula 46 connects to the outflow of the pump 42 and returns blood to the arterial system—in this case, via an anastomosis at the contralateral subclavian artery 14. So configured, blood is removed from the left ventricle 4 and returned to the systemic circulation, thus, directly assisting the left ventricle 4. A percutaneous wire 32 supplies power to the pump 42 via an externally worn motor controller and rechargeable battery system 30, as further illustrated in FIG. 2B.

As will be appreciated by one of ordinary skill, certain of the particular pump embodiments elsewhere herein shown and described in further detail are readily adapted for use in accordance with this presently illustrated method and configuration between component parts. This is particularly the case, for example, with respect to the embodiments illustrated in FIG. 4, FIG. 8, and FIG. 10 (and other figures further related to those embodiments).

The pump system, implant configuration, and surgical method shown and described by reference to FIGS. 1A-B are conducted without requiring anastomosis of inflow or outflow cannulas to major vessel walls. It is also to be appreciated that these non-anastomotic methods could be adapted to a mini-thoracotomy or thoracoscopic approach without the need for cardiopulmonary bypass or anastomosis of a vascular graft.

Figure 3A:
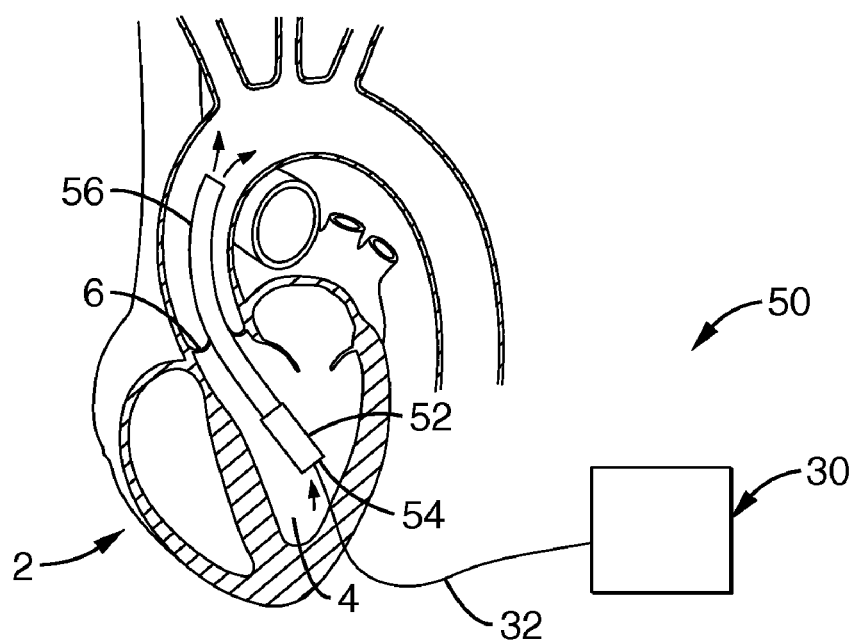

FIG. 3A shows a pump system 50 with a pump 52 that is positioned in a left ventricle 4 and with an outlet cannula 56 that is passed antegrade through the aortic valve 6. This surgical procedure could be implemented via a small thoracotomy. According to such a method, the pericardium is opened and traction is placed on the ventricular apex (not shown). Using puncture techniques and a dilator system, a thin walled trochar is then advanced into the ventricular cavity. The pump 52, such as a forward flow pump, is then advanced into the left ventricle 4 and the flexible outflow cannula 56 is readily advanced antegrade across the aortic valve 6. The pump 52 is then anchored at the ventricular apex using an anchor assembly, which may be chosen of suitable construction and operation in context with the system and methods described as apparent to one of ordinary skill.

The pump 52, so configured as just shown and described, draws blood through ports in the housing, such as shown for illustration at inlet 54, and pumps the blood forward through the outlet cannula 56 into the supravalvular aorta. The aortic leaflets would generally provide sufficient seal around the outlet cannula 56.

Figure 3B:
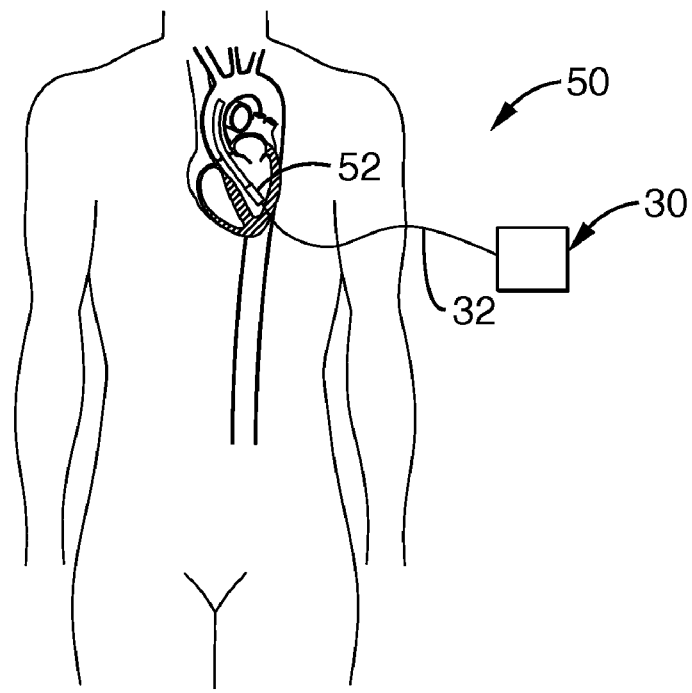

As shown in FIG. 3B, power is supplied to the pump 52 via a percutaneous wire 32 connected to an externally worn motor controller and rechargeable battery system 30.

As will be appreciated by one of ordinary skill, certain of the particular pump embodiments elsewhere herein shown and described in further detail are readily adapted for use in accordance with this presently illustrated method and configuration between component parts. This is particularly the case, for example, with respect to the embodiment illustrated by reference to FIG. 16.

According to further aspects of a pump system consistent with certain embodiments herein described, less invasive surgical insertion with a vascular anastomosis is performed via a small thoracotomy without cardiopulmonary bypass. Though not herein shown, for further illustration such method may proceed for example as follows.

The pericardium is opened and traction applied to the ventricular apex. Using puncture techniques and a dilator system, a thin walled inflow cannula is inserted into the left ventricle 4. The outflow graft may be anastomosed to the descending thoracic aorta. Alternatively, the outflow graft could be tunneled to the subclavian or femoral artery for anastomosis. A pump is then placed between the inflow and outflow grafts such that blood is removed from the left ventricle and pumped into the systemic circulation. The pump may be implanted in the thoracic cavity, or subcutaneously, or elsewhere as may be appropriate in a particular case or technique. A percutaneous wire provides power to the pump via an external controller and battery system.

Current left ventricular assist devices require surgical cannulation of the left ventricle via the ventricular apex and surgical anastomosis of an arterial graft to the thoracic aorta. The vast majority are too large for placement in the pericardial space or thoracic cavity and are implanted below the diaphragm in the anterior abdomen region. Subdiaphragmatic placement typically requires tunneling through the diaphragm to route the vascular grafts—this is a big operation and usually requires cardiopulmonary bypass. Two present LVADS are intended to be small enough to permit placement in the pericardial space, namely the LVAD marketed under the name "Jarvik 2000" and another LVAD named "HVAD™" previously investigated by Heartware, Inc. Placement of the pump in the pericardial space eliminates the need for diaphragmatic penetrations and minimizes the length of the pump inlet. A short pump inlet reduces the likelihood of thrombus formation in the pump. The Jarvik 2000 pump has been used in a modest number of patients. However, it is known to be hemolytic (rupture red blood cells) and requires almost twice the power of more efficient pumps such as the Heartware pump. The Heartware, Inc. pump has begun use in clinical trials, and proof of its safety and clinical benefit has not yet been demonstrated.

Various LVAD pump embodiments of the present disclosure are described more fully below. Each is considered to offer certain significant potential advantages over previously disclosed or used systems. Such improvements of the certain embodiments include, without limitation, one or more of the following: simplicity of design, reduction in cost, and reduction of power consumption over existing LVAD designs, and each could readily be adapted to conventional surgical insertion. Moreover, certain embodiments are considered to present the highly beneficial advantage of combining low profile, minimally invasive or less invasive delivery, with longevity of life as extended ambulatory implants.

1. Hollow Motor Shaft with Hydrodynamic Rotor Suspension

FIGS. 4-7 show various aspects of a present embodiment that features a pump 60 with first and second ends 62, 64, respectively, a housing 70, and a rotor 100. These components are configured in a particular manner relative to each other as follows.

Housing 70 includes a pump housing inlet section 72 adjacent to first end 62 coupled to a pump section 90 adjacent to second end 64. Pump housing inlet section 72 includes a tubular wall 74 with a tubular inner surface 76. Pump section 90 includes a centrifugal pumping chamber 92 with a pump outlet 94 aligned along a transverse axis T that is transverse to longitudinal axis L.

Figure 4:
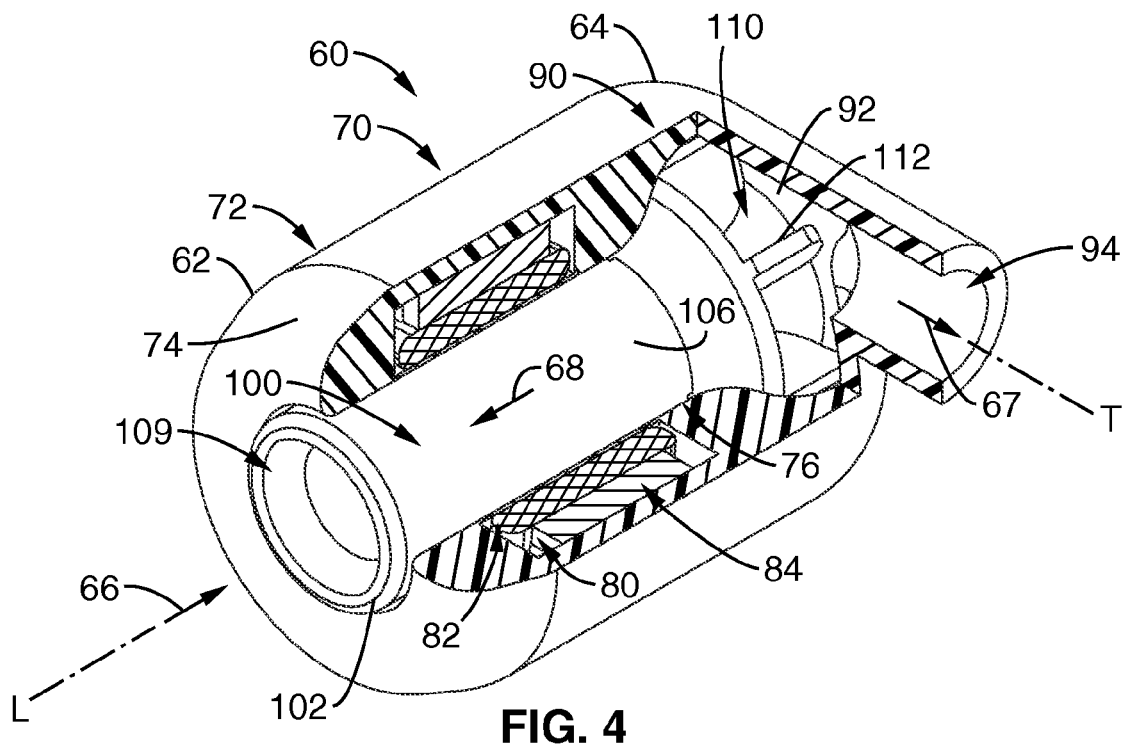
FIG. 4 shows a partially sectioned angular perspective view of a pump with a hollow motor shaft and hydrodynamic rotor suspension.
Figure 5:
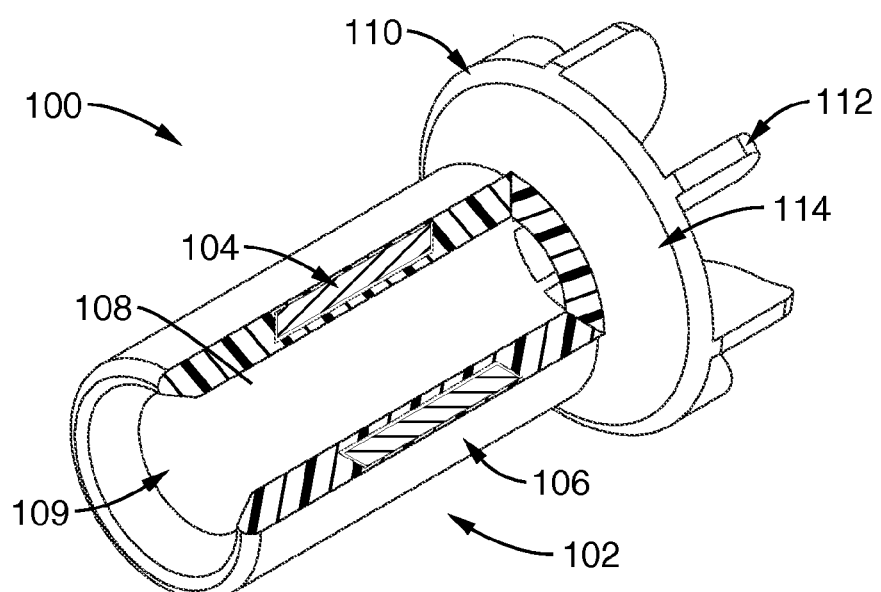
FIG. 5 shows a partially sectioned angular perspective view of the rotor of the pump in FIG. 4, revealing certain detail of the rotor including motor rotor magnets.

As shown in FIG. 4 and in finer detail in FIG. 5, rotor 100 includes a hollow shaft 102 and a pump impeller 110 extending from, e.g., is attached to or formed as an integral extension of, an end of shaft 102 located within pumping chamber 92. The hollow shaft 102 houses rotor magnets 104 for a radial flux gap motor. The cylindrical outer surface 106 of the hollow shaft constitutes a moving surface for a radial hydrodynamic bearing with inner surface 76 of pump housing inlet section 72. The bore 108 of the hollow shaft 102 acts as the inflow path for blood entering the pump 60 at the open inlet aperture or port 109 of bore 108 located at end 62 of pump 60. Such inflow blood path into inlet port 109 is schematically shown for further illustration by large bolded arrow 66 in FIG. 4.

This architecture of the present embodiment, according to the aspect providing a motor rotor integral to a forward shaft, provides considerable advantages and flexibility to the design. Previously disclosed LVAD pumps such as the Jarvik 2000, Heartmate II and DeBakey VAD employ axial flow hydraulics and, hence the flux gap of the respective motors are generally required to be relatively large because it also serves as the flow path of the blood. Consequently, motor efficiency is compromised. The flux gap of the present embodiment, however, is not the primary blood flow path and therefore can be much smaller and provide a more efficient motor. Placing the pump hydraulic elements, e.g., impellers, at the end of the shaft permits the use of pump hydraulics such as centrifugal and mixed flow rotors which are inherently more efficient at the flow regimes required for LVADS.

In addition, the outer diameter and length of the rotor shaft 102 can be readily adjusted to suit an appropriate parameter for a particular application to optimize motor performance and hydrodynamic bearing support for radial constraint of the rotating assembly.

Figure 6:
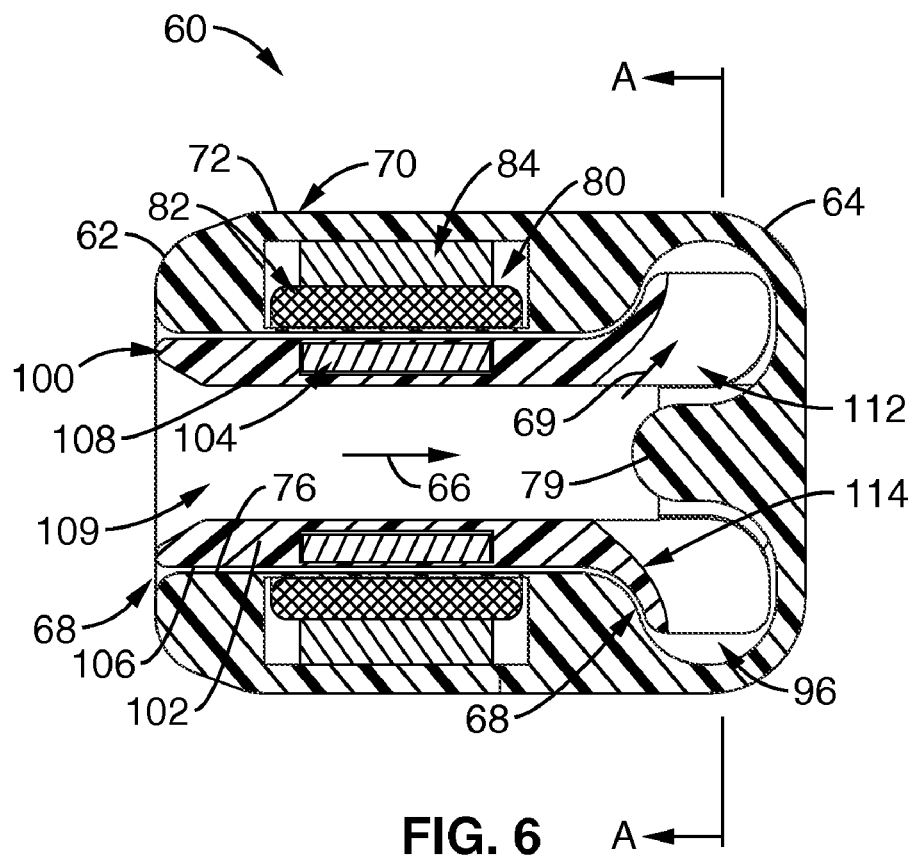
FIG. 6 shows an axially cross-sectioned side view of the pump shown in FIG. 4.

As further shown in FIG. 4 and FIG. 6, housing inlet section 72 further includes a motor stator 80 with coil windings 82 and backiron 84. Backiron 84 may be formed for example as laminations. A radial flux gap motor is provided, as electrical current passing through the coil windings 82 interacts with the magnetic flux of the motor rotor magnets 104 in the hollow shaft 102 of rotor 100 to produce torque on shaft 102, thus turning shaft 102 and impeller 110 of rotor 100. The motor in the embodiment shown is sensorless with back EMF commutation.

Impeller 110 includes a series of circumferentially spaced impeller blades 112 extending distally (e.g., in direction of flow) from an impeller shroud 114. Gaps between blades 112 are fluidly coupled to bore 108 of hollow shaft 102 of rotor 100, Impeller blades 112 are also configured such that, when turned, the action of impeller blades 112 push fluid contained therebetween circumferentially around longitudinal axis L and radially outward toward the outer periphery of pumping chamber 92, e.g., as indicated by flow path 69 along impeller blades 112 and at volute 96 in FIG. 6. Further shown in FIG. 6 is an inward protrusion 79 of housing 70 located generally centrally within pumping chamber 90. This aids in the hemodynamic flow between bore 108 and into the region of impeller blades 112 along flow path 69 in pumping chamber 90. While impeller blades 112 may extend radially beyond impeller shroud 75 from which they extend (or may terminate short of the shroud periphery), a radially flush orientation between these is considered present particularly beneficial hemodynamics in the chamber during pumping.

Figure 7:
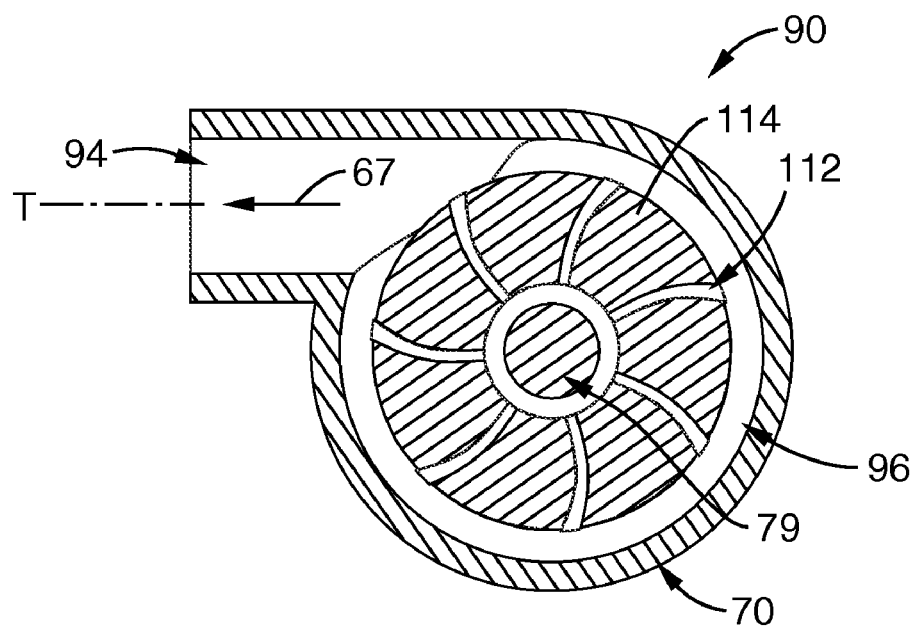
FIG. 7 shows a transversely cross-sectioned end view perpendicular to the axis of rotation at the level of the impeller of the pump shown in FIG. 4, such as taken along line A-A of FIG. 4 but through the whole pump assembly in that plane.

The rotating action of impeller blades 112 pushes blood circumferentially around and radially outward within pumping chamber 92, and expels the kinetic blood from the pump 60 through pump outlet 94 along path 67 (see FIGS. 4 and 7). This pushed flow within pumping chamber 92 also acts to pull blood from bore 108 into pumping chamber 92, which action furthermore pulls more blood into bore 108 through inlet port 109, thus providing a continuous cycle of flow through the pump. While a specific configuration and relative arrangement of such impeller blades 112 shown is considered of beneficial use, other more detailed designs may be employed as would be apparent to one of ordinary skill.

Radial support of the rotor assembly is provided by the action of the relative motion between the outer surface 106 of the hollow shaft 102 and the inner surface 76 of cylindrical bore 74 of the pump inlet section 72. This produces a hydrodynamic radial or journal bearing. This bearing beneficially minimizes shear stress and promotes leakage flow 68 from the pumping chamber 92 toward the inlet end 62 of the pump 60. Such leakage flow 68 is further driven by the highest pump pressure region located at volute 96 that communicates backward along the journal bearing clearance via a clearance path between the housing 70 and impeller shroud 114. All mating surfaces are in continual relative motion along the communicative leakage path backward along the pump 60 between housing 70 and rotor 100 toward proximal end 62 of pump 60. All such tight clearance, low flow surfaces are thus continuously washed with motion, and hemolysis and thrombosis can be minimized. Whereas several prior efforts have attempted to provide pumps with seals against leakage between primary blood flow path and other pump parts, the provision of this embodiment of active leakage flow path through moving parts uniquely allows active washing of exposed surfaces. This relieves the requirement for seals, which typically aggravate thrombus formation, and thus the present embodiments enhance longevity as an implant.

Figure 8:
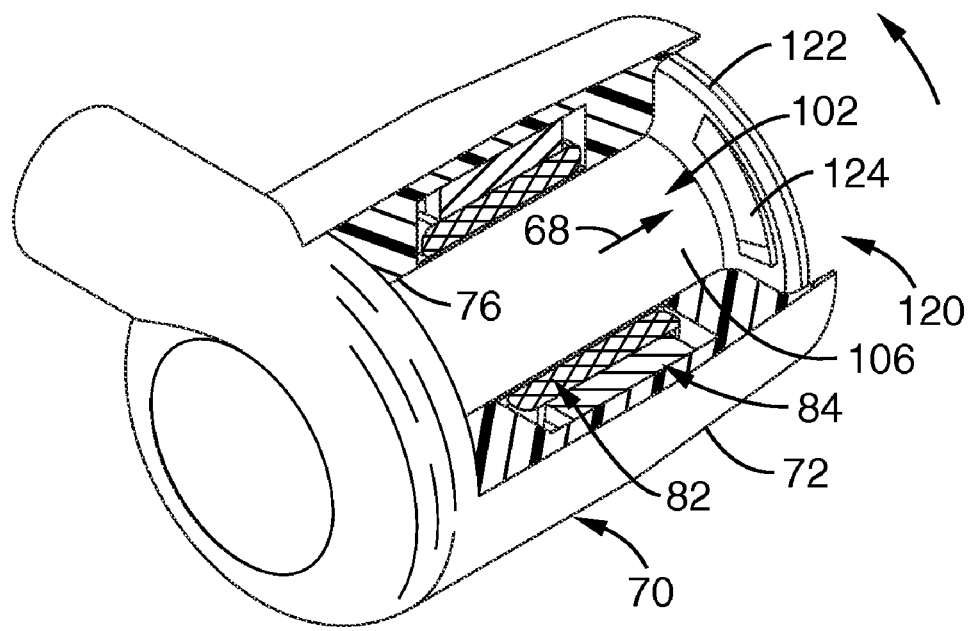
FIG. 8 shows a partially sectioned angular perspective view of another pump with a hollow motor shaft, hydrodynamic rotor suspension and a hydrodynamic thrust bearing at the pump inlet.
Figure 9:
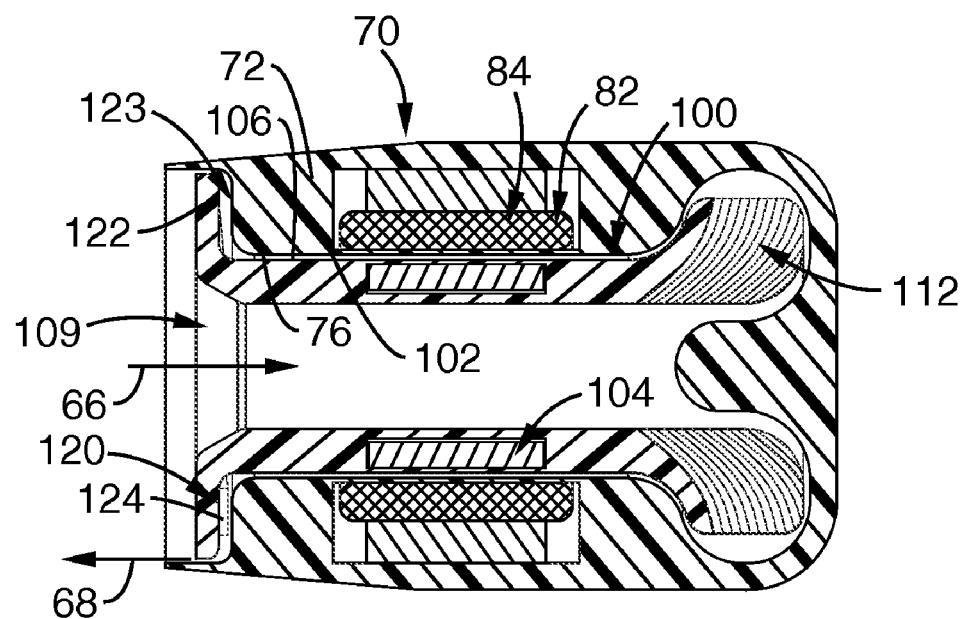
FIG. 9 shows an axially cross-sectioned side view of the pump shown in FIG. 8.

The magnetic attraction between the motor rotor magnets 104 and stator backiron 84 beneficially offset the axial hydraulic force produced by the spinning impeller 110. Alternatively, a hydrodynamic thrust bearing 120 may also be placed at the inlet end 62 portion of the hollow shaft 102, as illustrated in the further embodiment shown in FIGS. 8 and 9. If the thrust bearing features are integral with the rotor, they could be shaped to act as a pump as well as bearings. More specifically as shown in FIGS. 8 and 9, thrust bearing 120 includes an outwardly extending radial wall 122 extension from rotor shaft 102 fitted against a facing wall 123 of housing 70 with a certain gap clearance in fluid communication with the leakage flow path clearance between surfaces 76, 106 of housing 70 and rotor 100, respectively. One or more circumferential ramps 124 extend from wall 122 and toward facing wall 123 with a raised slope angled away from the axis of rotation for rotor 100. By rotor's spinning motion, these raised ramps 124 spin around the axis of rotation through the gap between respectively facing walls 122,123. The resulting pumping action enhances leakage flow 68 through the journal bearing clearance between respectively facing surfaces 76, 106.

For further illustration and understanding, a pump consistent with the present embodiment may be adapted for a nominal flow of about five LPM, and such more specific embodiment may be for example about 0.9" in diameter and 1.30" in length, weigh approximately 50 grams, and would displace about 15 cc's. Power consumption at five LPM and 100 mm Hg may be about 5 watts.

Among other benefits, the present embodiment allows for a size envelope that is well suited for insertion into the left ventricular apex or atrium via a mini-thoracotomy and would occupy very little extra-cardiac volume. A vascular graft from the pump outlet would typically be anastomosed to an aorta or a subclavian artery.

The pump according to the present embodiment may also be constructed small enough that it could be located on the anterior chest wall and receive blood from a transthoracic cannula to the left heart and return flow to the circulation via a graft to the subclavian artery. Access to the left ventricle could also be achieved with a thin-walled cannula placed via the subclavian artery, retrograde across the aortic valve. The aortic valve leaflets would seal around the wall of the cannula. Pressurized flow from the pump outlet could be returned to the circulation via a graft to a peripheral artery such as the subclavian. Such a procedure would be in the domain of the interventional cardiologist.

2. Hollow Motor Shaft with Jeweled Bearing Rotor Suspension

Figure 10:
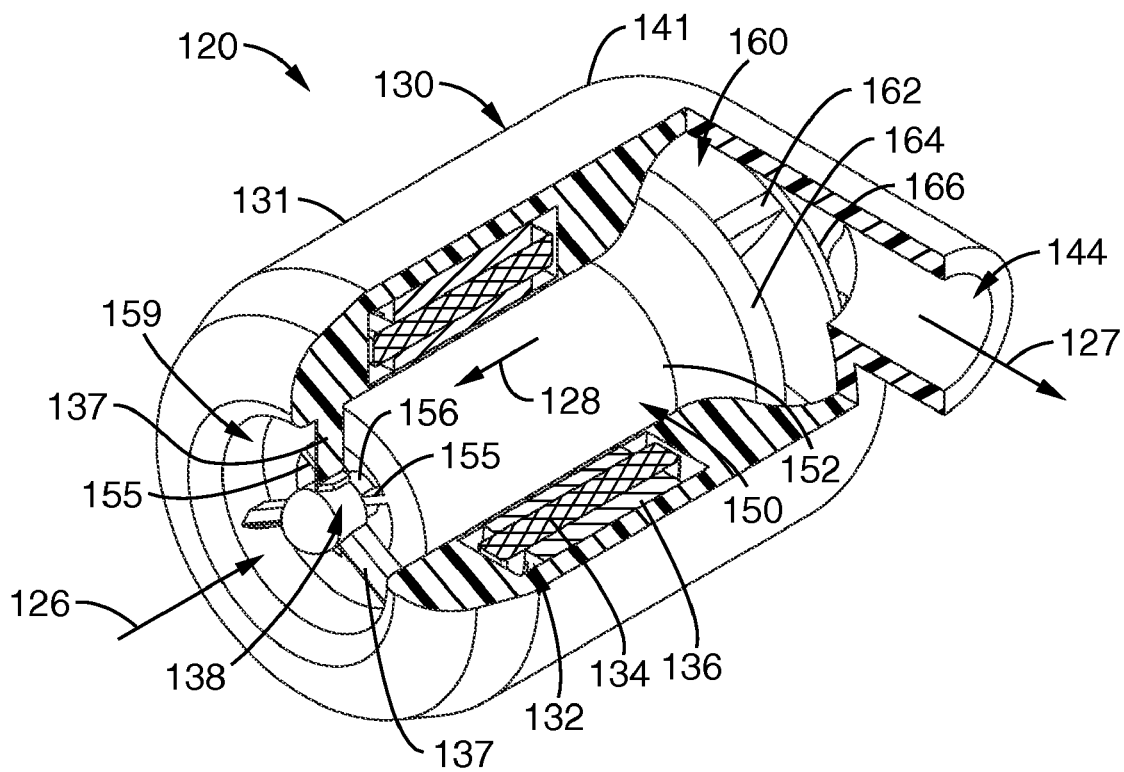
FIG. 10 shows a partially sectioned angular perspective view of another pump with a hollow motor shaft with jeweled bearing rotor suspension.
Figure 11:
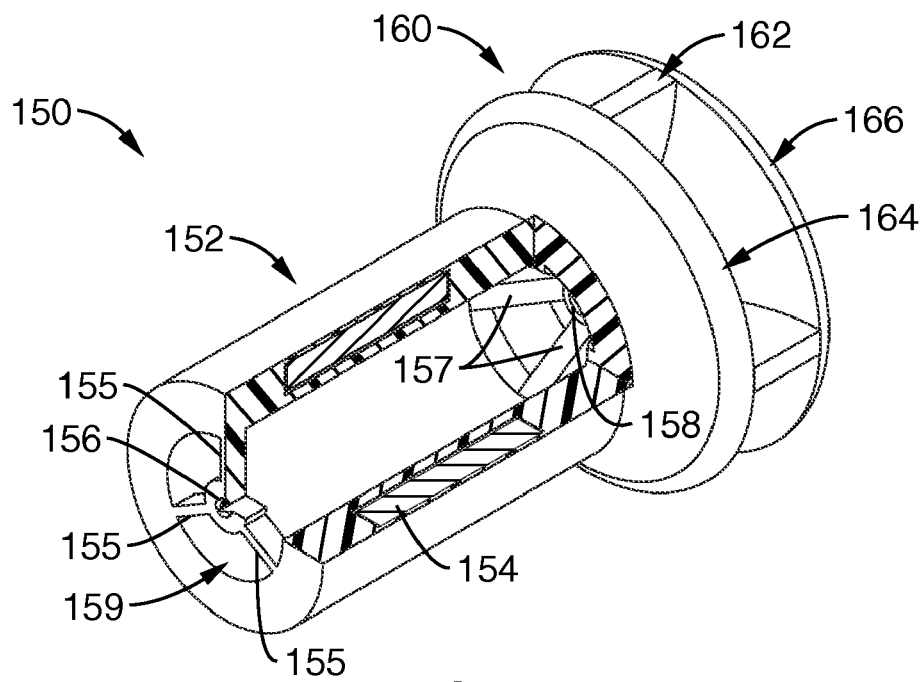
FIG. 11 shows a partially sectioned angular perspective view of the rotor of the pump shown in FIG. 10, and reveals certain details of the rotor including the motor rotor magnet.
Figure 12:
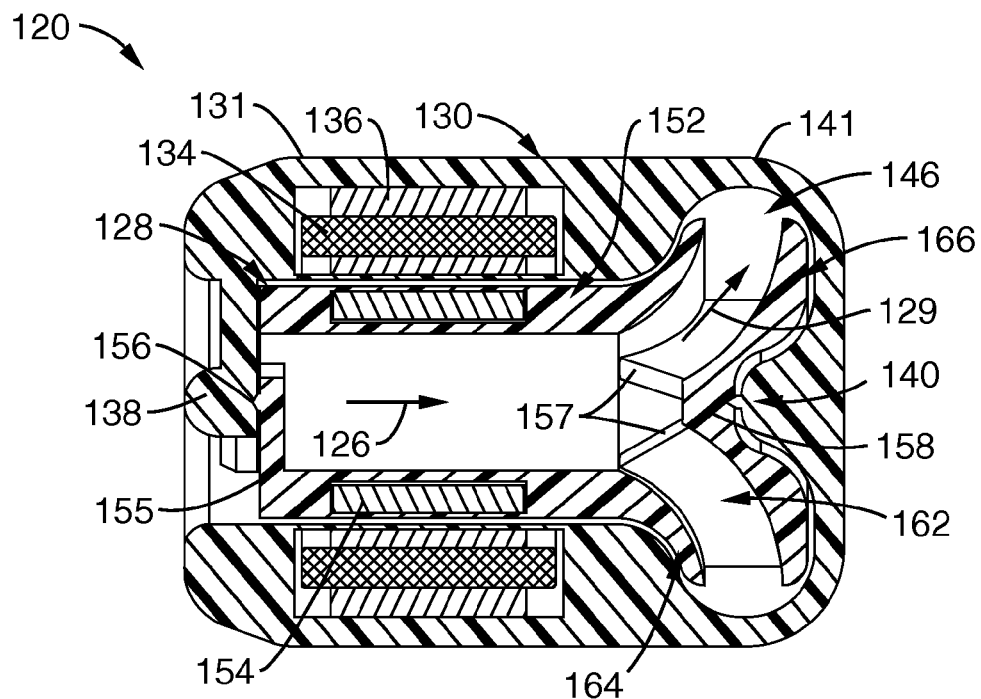
FIG. 12 shows an axially cross-sectioned side view of the pump shown in FIG. 10.

FIGS. 10-12 show another pump 120 that includes a housing 130 and a rotor 150, which are described in further detail as follows.

Rotor 150 is comprised of a hollow shaft 152, one end of which is attached to the pump impeller 160. The hollow shaft 152 also houses the rotor magnets 154 for a radial flux gap motor. Pivot bearing elements 156, 158 are supported at each end of the hollow shaft by struts 155,157 attached to the wall of the shaft 152 and extending inward within its bore. Blood enters the pump 120 through the bore inlet 159 into the hollow shaft 152. Impeller 160 includes impeller blades 162 located between an impeller shroud 164 and an impeller hub 166. The internal blood flow through the pump rotor 160 is shown in FIG. 12 at path 126, and at path 129 as it enters the pumping section 141 of housing 130 into impeller 160 within open regions bound by impeller blades 162, shroud 164, and hub 166. Rotation of impeller 160 forces blood centrifugally around pumping section 141 including into volute space 146, and ultimately out from the pump 120 via outlet flow path 127 at outlet 144.

This particular impeller arrangement of the present illustrative embodiment may be combined into other pump embodiments of the current disclosure as alternatives thereof. Moreover, the current pump embodiment may instead incorporate other specific impeller constructions, such as for example those shown in previous embodiments above.

This architecture of the present embodiment, with a motor rotor integral to a forward shaft, provides considerable advantages and flexibility to the design. Designs such as the Jarvik 2000, Heartmate II and DeBakey VAD employ axial flow hydraulics and, hence the flux gap of the motor must be large because it also serves as the flow path of the blood and motor efficiency is compromised. Conversely, present embodiments provide a flux gap that is not the primary blood flow path and can, hence be much smaller and provide a more efficient motor. Placing the pump hydraulic elements to the end of the shaft permits the use of pump hydraulics such as centrifugal and mixed flow rotors which are inherently more efficient at the flow regimes required for LVADS.

As shown in FIGS. 10 and 12, pump housing 130 includes an inlet portion 131 and a pumping section 141. A motor stator 132 with coil windings 134 and backiron laminations 136 is located in the inlet portion 131 of the pump housing 130. Current passing through the coils of motor stator 132 interacts with the magnetic flux of the motor rotor magnets 154 to produce torque, thereby turning rotor 150. The motor is sensorless with back EMF. The pivot bearing features 156, 158 carried by the hollow shaft 152 of rotor 150 would mate with matching pivot bearing features 138, 140, respectively carried by the pump housing 130. The housing pivot bearing features 138 at the inlet 159 are supported by struts 137 attached to the bore of the inlet section 131 of the housing 130. The pivot bearing feature 140 at the rear would be placed at the axis of the rear of the housing 130. The attraction between the motor rotor magnet 154 and motor stator 132 could offset the hydraulic axial force produced by the impeller 162.

The clearance between the outer diameter of the hollow shaft 152 and the bore of the housing 130 at pump inlet 159 would be large enough to minimize hydrodynamic bearing action and drag. Good washing of the pivot bearing areas and sufficient leakage in the clearance between the rotor shaft 152 outer diameter and inner bore of the housing, such as shown in FIG. 10 in part at leakage path 128, will avoid thrombosis.

In one particular example of overall dimensions, a pump with a nominal flow of five LPM would be about 0.9" in diameter and 1.50" in length weigh 60 grams and would displace about 17 cc's. In one particular further embodiment of use, the envelope of this particular embodiment (e.g., such as with such exemplary dimensions just described) could be inserted into the left ventricular apex or atrium via a mini-thoracotomy and would occupy very little extra-cardiac volume. A vascular graft from the pump outlet would be anastomosed to the aorta or the subclavian artery. The pump is also small enough that it could be located on the anterior chest wall and receive blood from a transthoracic cannula to the left heart and return flow to the circulation via a graft to the subclavian artery. Likewise, access to the left heart could be achieved with a thin-walled cannula placed via the subclavian artery, retrograde across the aortic valve left and flow returned to the circulation via a graft to the subclavian artery.

Further to the various aspects of the present embodiment just described above, it is to be appreciated that the present pump 120 provides a hollow shaft rotor motor with axial inlet flow 126 flowing through the hollow bore of a rotor motor rearwardly along the pump, and leakage flow 128 flowing in reverse displacement to the inward flow in a bearing clearance between the rotor and motor in the housing. Both the axial inlet flow, rotor motor, and reverse axial leakage flow, are positioned forward of a centrifugal pump with transversely displaced outlet flow 127 at the rear of the pump. While certain other features differ between the embodiments, these aspects just described are similarly found in the embodiment variously shown and described by reference to FIGS. 4-7.

3. Solid Shaft with Radial Rear Pump Inlet and Hydrodynamic Suspension

Figure 13:
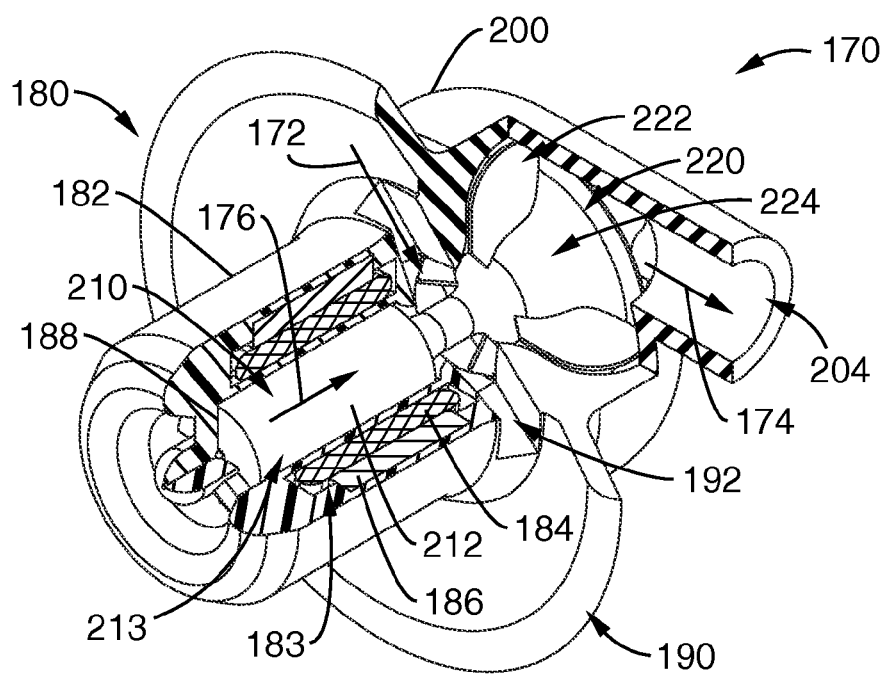
FIG. 13 shows a partially sectioned angular perspective view of another pump with a solid shaft, radial rear pump inlet, and hydrodynamic suspension.
Figure 14:
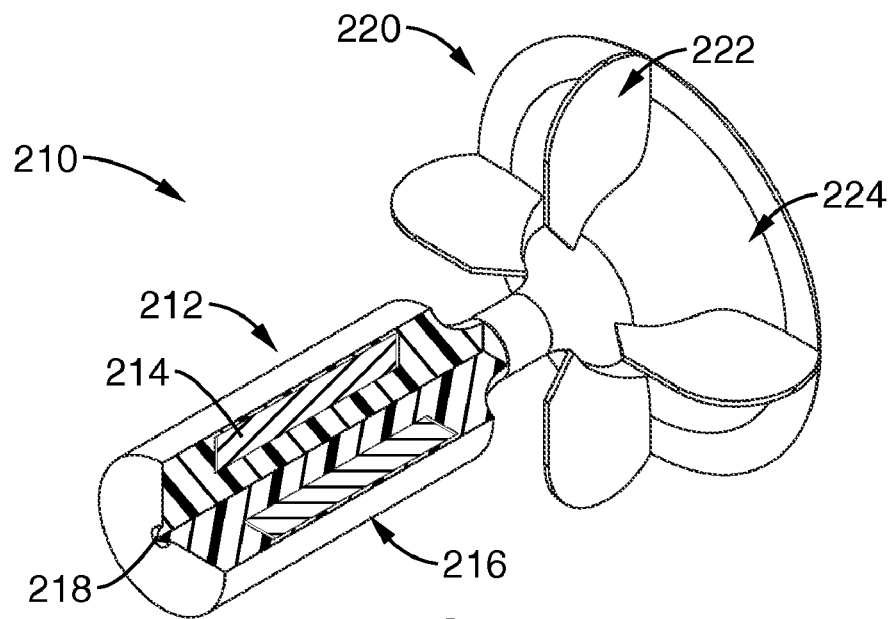
FIG. 14 shows a partially sectioned angular perspective view of the rotor of the pump shown in FIG. 13, revealing certain details of the rotor such as the motor rotor.
Figure 15:
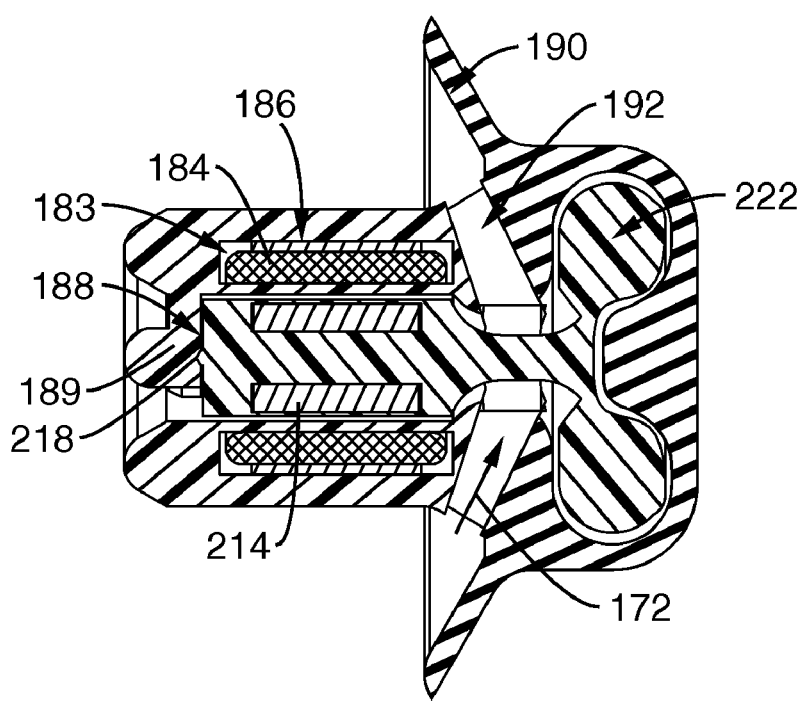
FIG. 15 shows an axially cross-sectioned side view of the pump shown in FIG. 13.

FIGS. 13-15 show certain aspects in varying levels of detail of a pump 170 that displaces the pump inlet to the rear in a radial array compared to certain of the previous embodiments above. The impeller 220 is integral with a solid shaft 212 of the motor rotor 210. The solid shaft 212 houses the magnets 214 of the motor rotor. Located in the main housing (FIG. 13 and FIG. 15) are the motor stator 183, including coil windings 184 and backiron laminations 186. Current moving in the coils 184 interacts with the flux of the motor rotor magnets 214 to produce torque, thereby turning rotor 210. Sensorless back EMF commutation is employed.

This present embodiment is also distinct from certain other embodiments disclosed hereunder in that the inlet flow 172 enters the pump 170, radially, to the rear of the motor 183 through inlet ports 192 in the pump housing 180. This is accomplished in the particular illustrative embodiment shown by aid of a flexible pump inlet cowling 190 that circumscribes the pump 170 and guides blood to inlet ports 192. Radial constraint of the rotor 210 is achieved by hydrodynamic forces produced by the relative motion of the rotor shaft 212 and the bore of inlet portion 182 of the pump housing 180. Passive magnetic axial force is produced by the attraction of the motor rotor magnets 214 to the stator backiron 186.

This architecture of the present embodiment, with a motor rotor integral to a forward shaft, provides considerable advantages and flexibility to the design. Designs such as the Jarvik 2000, Heartmate II and DeBakey LVAD employ axial flow hydraulics and, hence the flux gap of the motor must be large because it also serves as the flow path of the blood and motor efficiency is compromised. The flux gap of this invention is not the primary blood flow path and can, hence be much smaller and provide a more efficient motor. Placing the pump hydraulic elements to the end of the shaft permits the use of pump hydraulics such as centrifugal and mixed flow rotors which are inherently more efficient at the flow regimes required for LVADS.

It is to be appreciated that the outer diameter and length of the shaft can be readily adjusted during the design for specific implementations to optimize motor performance and hydrodynamic bearing support for radial constraint of the rotating assembly.

The location of the displaced inlet 192, when inserted into the ventricular cavity, may be prone to obstruction by the ventricular wall due to a 'sucking down' effect of the pump. Such a difficulty could be prevented by using a cowling 190 as shown in FIG. 13 that would serve to keep the ventricular wall away from the pump inlet 192.

The following further features are shown variously among the present FIGS. 13-15. A jeweled bearing interface 188 between rotor 210 and housing 180 and that includes gaps for blood flow. A blood leak flow path 176 is driven through a radial hydrodynamic bearing clearance 213 located between the outer hydrodynamic bearing surface 216 of rotor shaft 212 and an inner bore surface of pump housing inlet portion 182. This jeweled bearing 188 includes a pivot bearing interface between forward pivot bearing feature 218 of rotor 210 that mates with pivot bearing feature 189 of housing inlet portion 182. Leakage flow 176 travels rearward along the bearing clearance 213 to combine with inlet flow 172 toward and into pumping section 200 of housing 180 where impeller 220 is located.

Impeller 220 includes impeller blades 222 and impeller hub 224, though other specific impeller constructions may also be used. Impeller 220 provides centrifugal pumping around pumping chamber 200 to expel kinetic blood out from pump 170 along outlet path 174 through outlet 204. It is to be further appreciated as a further feature to the present embodiment, or other present embodiments, that a thrust bearing may also be included as a booster pump to enhance the leakage flow shown and described. Such may be, for example, similar to other thrust bearing(s) elsewhere herein shown and described, as may be appropriately adapted or modified according to one of ordinary skill to appropriately integrate with the other features of the particular overall embodiment.

Further to the various aspects of the present embodiment just described above, it is to be appreciated that the present pump 170 provides a solid rotor motor and thrust bearing-enhanced axial leakage flow 176 positioned forward of a radially displaced inlet flow path 172, which are both located forward of a circumferential pump with transversely oriented outward flow 204 path.

The combination of features of the current embodiment is generally suited for direct placement in the left ventricle or atria, though radially enlarged features if appropriately constructed or otherwise modified to be collapsed during delivery may allow for more reduced profiles for minimally or less invasive delivery. It is to be appreciated that the next two embodiments, which represent further modifications of the current embodiment in certain regards, offer a great deal of flexibility in terms of adaptation to minimal and less invasive implantation.

4. Forward Flow Pump with Axisymmetric Shape for Trochar Insertion into Left Ventricle The pump 230 of the embodiment shown in FIGS. 16-17 employs a same or similar rotor 270 with integral attachment of a solid rotor shaft 272 to the impeller 280 as the previous embodiment shown in FIGS. 13-15. The motor rotor is the solid shaft 272 and is radially constrained with hydrodynamic suspension. Additional features shown include a jeweled bearing interface 288 between rotor 270 and housing 240, with gap clearances between moving parts that are fluidly coupled to a hydrodynamic bearing clearance 273 between an outer surface of rotor shaft 272 and inner bore of forward section 242 of housing 240. These clearances allow for leakage flow 236 to actively wash the respective moving surfaces. As stated elsewhere herein, a thrust bearing may also be provided (though not shown) as a booster pump to enhance the leakage flow 236.

Also shown variously in these present figures are motor stator coil 244 and motor stator backiron 246 that provide a flux gap motor with motor rotor magnet 274. An inlet blood flow path 232 enters pump 230 through inlet ports 252 located rearward of the rotor motor coupling. Impeller 280 includes impeller blades 282 and an impeller hub 284.

Figure 16:
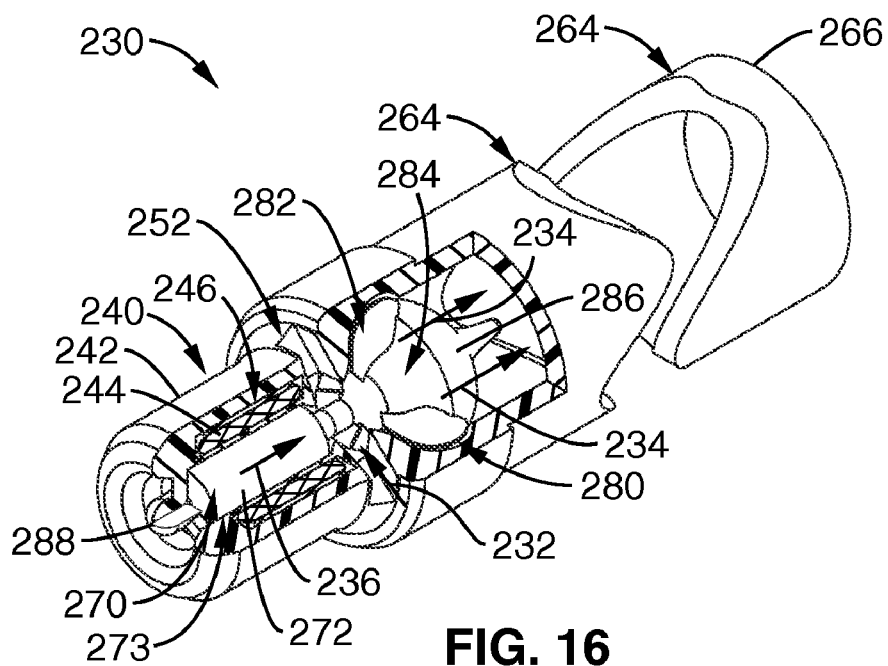
FIG. 16 shows a partially sectioned angular perspective view of a forward flow pump with generally axisymmetric shape adapted for less invasive trochar insertion into the left ventricle.
Figure 17:
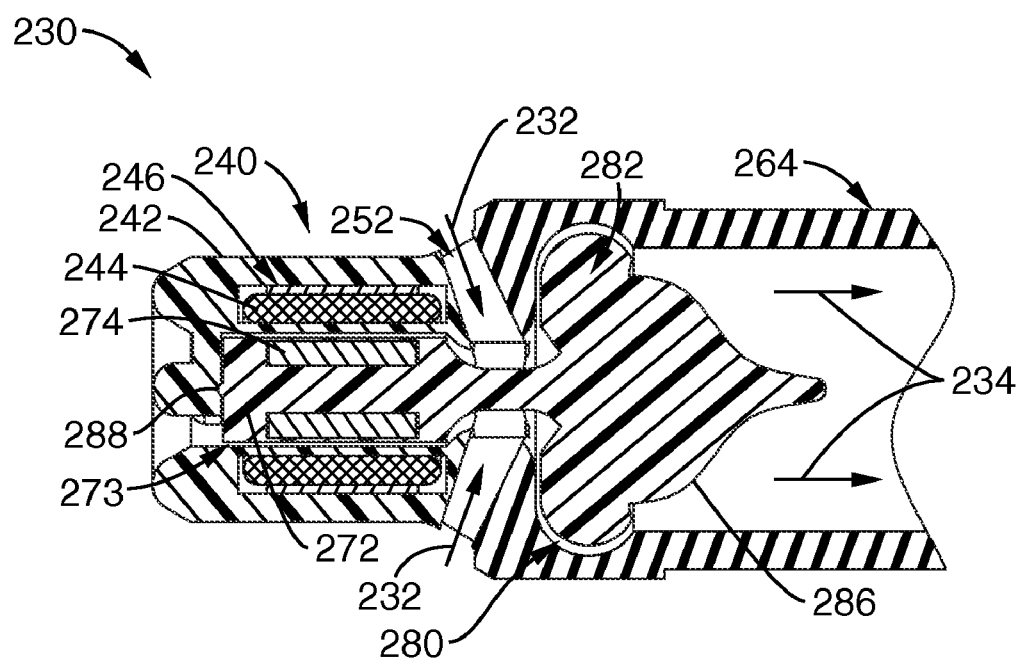
FIG. 17 shows an axially cross-sectioned side view of the pump shown in FIG. 16.

The present embodiment differs from certain other embodiments herein shown and described, in that the outflow 234 from the impeller 280 is generally axial, e.g., is parallel in the illustrative embodiment shown, rather than transverse or perpendicular to the axis of rotation of the pump as per the prior embodiment above. As shown in FIG. 16 and FIG. 17, the outflow path 234 is directed through a flexible outflow cannula 264. As also shown, a flow director 286 may be further provided by impeller assembly 280 to enhance this axial outflow 234 axially through outflow cannula 264.

Further to the various aspects of the present embodiment just described above, it is to be appreciated that the present pump 230 provides a solid rotor motor and axial leakage flow 236 positioned forward of a radially displaced inlet flow path 232, which are both located forward of an axial outward flow 234.

The construction of this present embodiment and resulting forward axial flow is particularly well adapted for complete implantation of the pump without the need for a vascular anastomosis. One example of such method of use that is considered of particular benefit is described for further illustration as follows, and relates for example to a similar procedure as that herein shown and described by reference to FIGS. 3A-B.

More specifically, the tip 266 of the outflow cannula 264 is inserted through a small hole in the ventricular apex and the outflow cannula passed antegrade across the aortic valve such that the tip of the cannula was above the aortic valve. The aortic valve leaflets would seal around the cannula wall. The outflow cannula could be reinforced or, possibly an inflatable pantaloon design to minimize abrasion of the valve leaflets. The cannula diameter could be much smaller than the pump body. The outer diameter of the outflow cannula as it traverses the aortic valve could be for example approximately 7 mm. The main body of the pump with the pump inlet would remain in the left ventricle. During pump operation blood would be pump from the left ventricle into the supravalvular aorta.

5. Rear Flow Pump with Axisymmetric Shape for Peripheral Arterial Insertion

Figure 18:
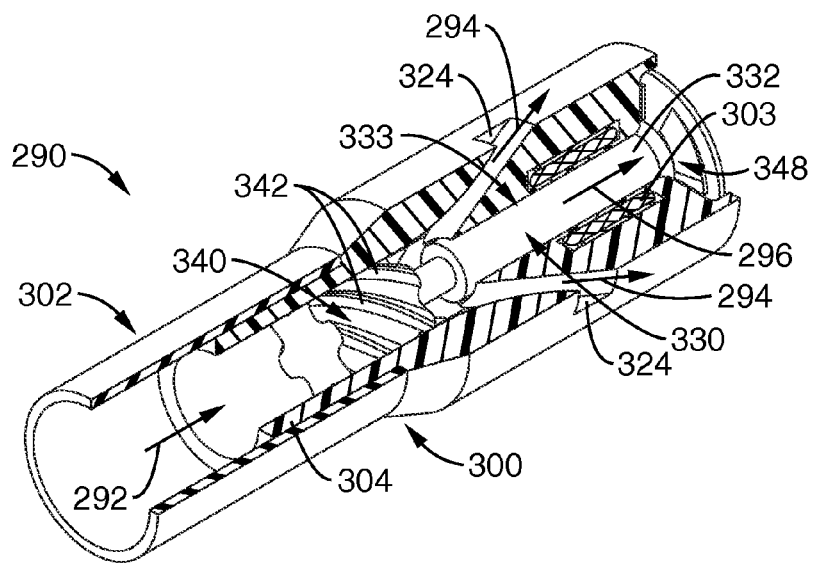
FIG. 18 shows a partially sectioned angular perspective view of a rear flow pump with generally axisymmetric shape adapted for minimally invasive peripheral arterial insertion.
Figure 19:
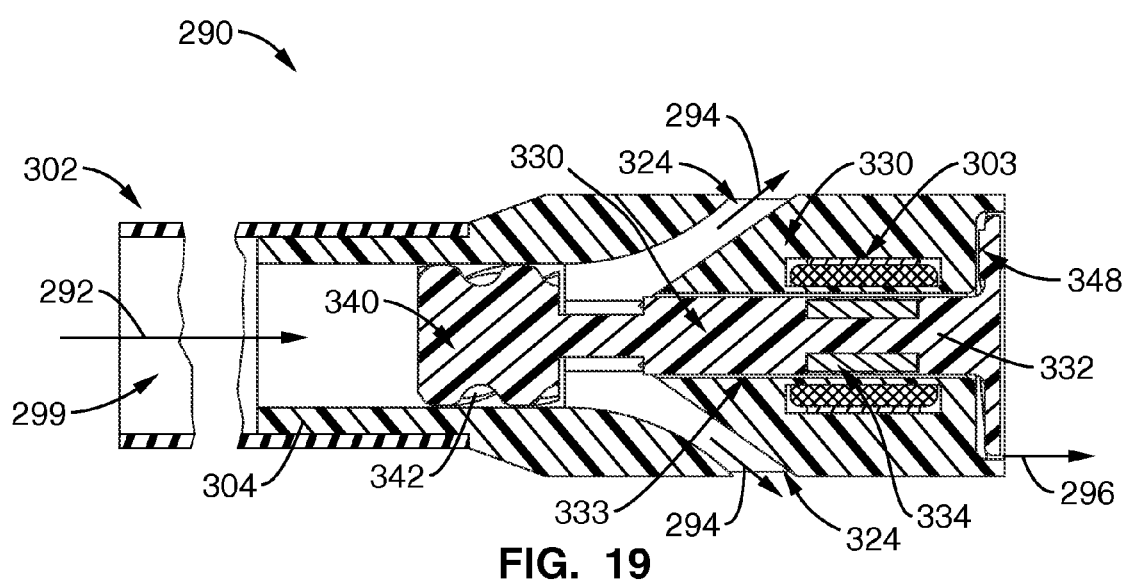
FIG. 19 shows an axially cross-sectioned side view of the pump shown in FIG. 18.

FIGS. 18-19 show a pump 290 according to another embodiment that uses a similar rotor 330 with integral attachment of the solid rotor shaft 332 to an impeller 340, and similar principle of hydrodynamic suspension and motor operation, as shown and described by the immediate preceding embodiment of FIGS. 15-17. The solid rotor shaft 332 comprises rotor magnets 334 that interact with motor stator 303. Similarly, a flexible cannula 302 is attached to the pump body or housing 300. However, according to the present embodiment, different hydraulic pumping elements are employed to reverse the flow direction relative to the axial flow cannula 302 and radially displaced flow ports 324. Hence, the tip of the cannula 302 would be the pump inflow, as shown at inflow path 292 through inlet port 299, and the radial slots or ports 324 would serve as the pump outlet, as shown at outlet flow path 294.

Further more detailed aspects of the specific illustrative embodiment shown in FIGS. 18-19 include the following. Impeller 340 includes a particular arrangement with helically disposed outer beveled surface extensions that provide impeller blades 342 that function during rotation as an axial flow or mixed flow pump. A thrust bearing 348 includes a wall that is transverse to the axis of rotation with raised surface extensions or ramps pointing inward into a clearance between the transverse wall and housing 300. This clearance housing the thrust bearing pumping ramps is fluidly coupled to hydrodynamic bearing clearance 333, and is thus integral to leakage flow path 296. Rotation of rotor 330 turns thrust bearing 348 to counteract axial forces and to enhance the leakage flow 296 out from pump 290 at its rear.

In addition, inlet cannula 302 is shown as a tubular member secured onto a tubular inlet extension 304 of otherwise integrally constructed housing 300. Housing 300 may be constructed of strong, robust material, whereas cannula 302 may be a more flexible polymeric or other elastomeric material, and they may be secured according to various methods known to one of ordinary skill, such as heat bonding, adhesive bonding, welding, solvent bonding, mechanical interface, etc.

Further to the various aspects of the present embodiment just described above, it is to be appreciated that the present pump 290 provides axial inlet flow 292 forward of radially displaced outlet flow 294, which are both forward of the motor and of the leakage flow 296 that is axial with the inlet flow 292 and enhanced or "boosted" by a pumping thrust bearing 348 located rearward of the other features of the pump 290.

This configuration of the present embodiment could be adapted in certain specific implementations to emulate the function and method of insertion of the temporary Hemopump® but would have the advantage of very long life for chronic implantation, and may be constructed for example at about 6 mm in diameter. This device of the present embodiment would be adapted for insertion in the subclavian artery such that the tip of the inflow cannula would reside in the left ventricular cavity and the radially placed outflow ports located distal to the aortic valve. The valve leaflets would seal against the wall of the inflow cannula. The electronics for the motor could be subcutaneously implanted adjacent to the arterial insertion site or worn externally with a battery pack. This arrangement may be similar for example to that shown in FIGS. 2A-B.

It is also contemplated that the pump 290 of the current embodiment may be modified as to method of use to turn the rotor in an opposite circumferential direction, which would reverse all aspects of flow through the pump. In this setting, ports 324 would be radially displaced inlet ports, vs. outlet ports, and flow path 294 would be inlet flow reversed of the outlet flow arrows shown. Flow path 292 through inlet cannula 302 would be reversed as outlet flow through cannula 302 as an outlet flow cannula. However, according to this particular reverse orientation of flow, the principal modification that would be desired would be to reverse the orientation of ramped extensions on the thrust bearing 348 to instead ramp in the reverse direction of turning that bearing. In this reverse orientation, the rotor motor and thrust bearing-enhanced leakage flow would be located rearward of radially displaced inlet flow and outlet flow that would be axial to the leakage flow.

6. Centrifugal Impeller with Axial Flux Gap Motor

Figure 20:
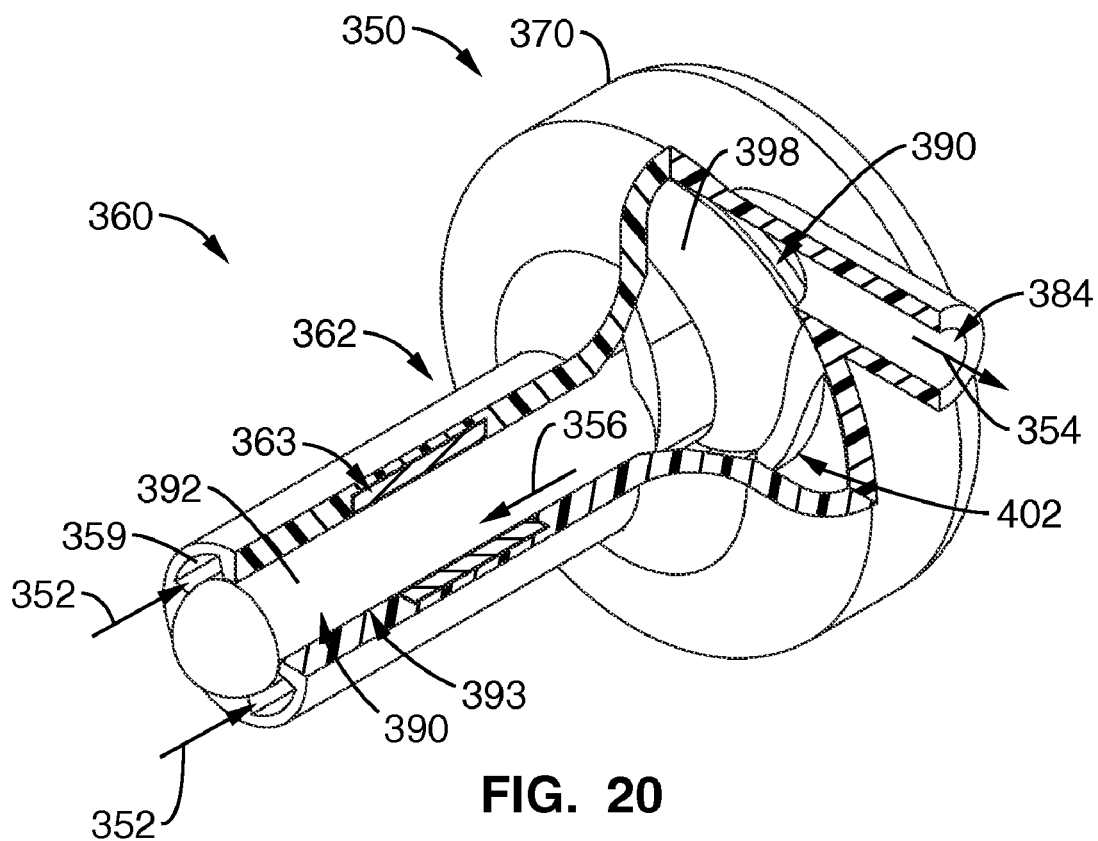
FIG. 20 shows a partially sectioned angular perspective view of a centrifugal pump with an axial flux gap motor.
Figure 21:
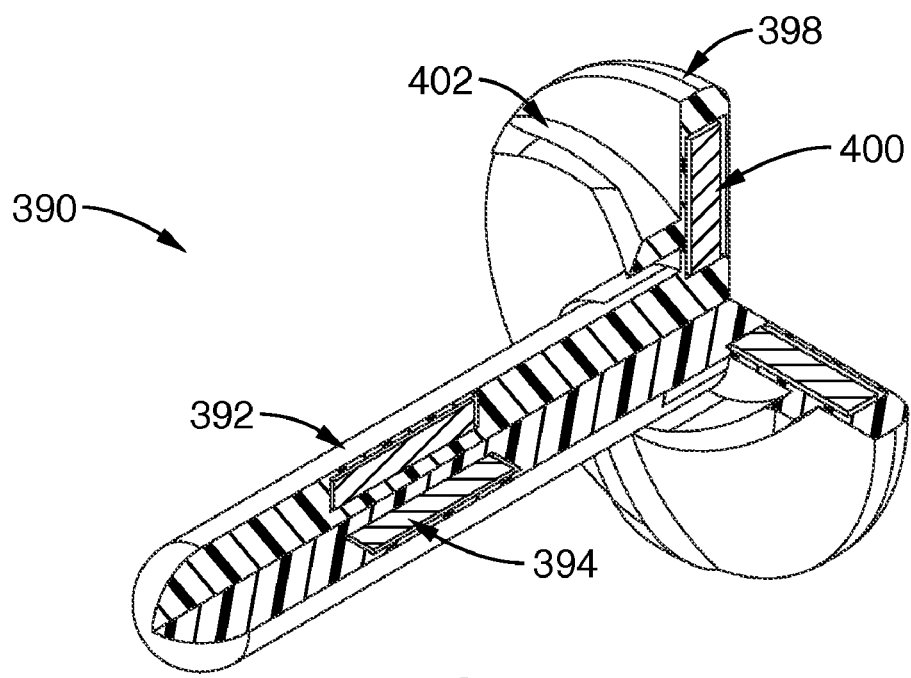
FIG. 21 shows a partially sectioned angular perspective view of the rotor of the pump shown in FIG. 20, revealing certain details of the rotor including bearing and motor magnets.
Figure 22:
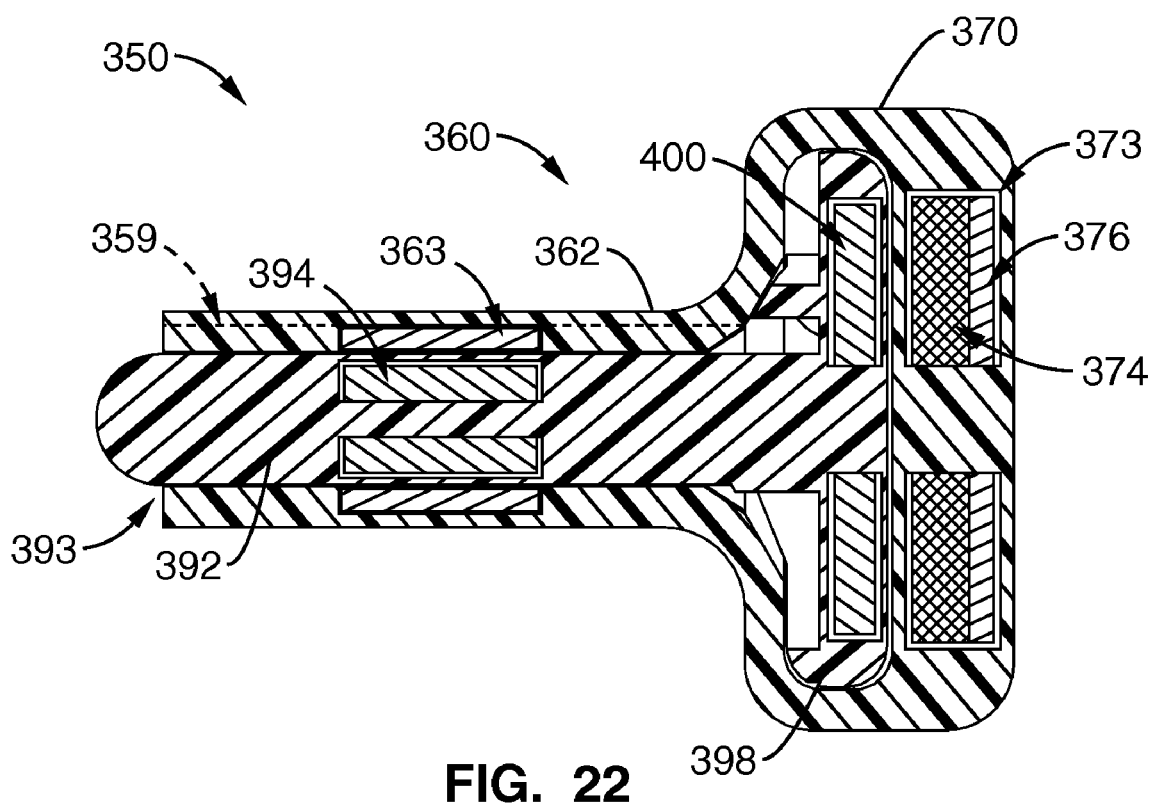
FIG. 22 shows an axially cross-sectioned side view of the pump shown in FIG. 20.

FIGS. 20-22 show another embodiment for a pump 350 that employs a rotor 390 with an integral disc shaped impeller 398 coupled to a pumping chamber 370 of a housing 360, and with a solid shaft 392 extending within a tubular inlet portion 362 of housing 360. Torque transmission is achieved with an axial flux gap motor. The motor rotor 400 is comprised of magnets placed in a disc shaped impeller structure 398 on which reside the impeller blades 402. One end of the rotor shaft 392 is attached to the impeller disc 398. Located in the housing 360 (FIG. 22) is the motor stator 373 with stator backirons 376 and coil windings 374. As in previous designs described in the present disclosure, the shaft 392 of rotor assembly 390 is suspended by hydrodynamic action in the space 393 between the outer surface of the shaft 392 and the bore of the housing inlet portion 362. Inlet flow area for the pump inlet is provided by large area grooves as shown as inlet 359 in FIG. 20, and in shadow in FIG. 22. The radial hydrodynamic bearings would be lobed, rather than cylindrical—a standard practice in the design of journal bearings. A hollow shaft could also be used to provide the inlet area. The axial flux gap motor will result in relatively large axial loads resulting from the magnetic attraction of the motor rotor magnets 400 to the stator backiron 376. This can be offset by passive axial magnetic bearings with magnets 394 residing in the rotor shaft 392 and the appropriately registered magnets 363 located along inlet section of the housing. It is to be appreciated that, while specific dimensions may vary as to the specific implantation and constructions chosen consistent with the present embodiments, the outer diameter of the pump housing according to the present embodiment may be about 50% larger than previously described embodiments of the present disclosure—e.g., may be about 1.6" in one particular example. The weight of such a pump may be for example about 90 grams.

Thus, the inlet path is shown at 352, and the flow path proceeds through the inlets 159, and rotation of impeller blades 402 forces the blood around out through flow path 354 at outlet 384. Leakage flow proceeds along path 356 in space 393.

This present embodiment, while providing certain highly beneficial features and results that may be appropriate in many settings, also offers limited flexibility in terms of adaptation to minimally and less invasive implantation compared to other present embodiments. This is because of certain geometrical constraints of this specific approach, such as in particular radially enlarged geometry generally concomitant with the flux gap motor employed at the centrifugal pump impeller. However, this present embodiment remains well suited for direct placement into the left ventricle or atria.

7. Novel Methods and Devices for Less Invasive Cannulation of the Chambers of the Heart It is to be appreciated that the reduced size and power utilization provided by the present embodiments allow certain novel methods to be employed for cannulation of a chamber of the heart.

In one particular illustrative regard, the basic approach to cannulation involves the following basic steps and supporting devices:

1. Surgical or thoracoscopic exposure of the heart to provide visualization and ready access for manipulation.
2. A means for applying traction to the wall of the intended heart chamber to facilitate incising the heart or inserting an introducer system.
3. A means for controlling blood loss from the site of heart chamber access.
4. Needle and wire guides to establish initial access to the heart chamber.
5. A removable dilation system to establish a tract in the wall of the heart chamber to permit introduction of an inflow cannula or pump into the heart chamber.
6. A means for mechanically fixing the cannula or pump to the wall of the heart chamber.

Existing surgical and thoracoscopic techniques are very effective in achieving exposure of the heart and the walls of the heart chambers. Following exposure of the heart, the pericardium is typically required to be opened to provide direct access to the surface of the heart.

The surgical method, wherein the left ventricle is compromised, places the patient on heart lung bypass, while a coring tool or scalpel is used to remove a plug of tissue in the heart. This is typically followed by insertion of an apical tube into the ventricle. Applying traction to the wall of a heart chamber is presently done by placing stitches into the myocardium (heart muscle), usually with felt pledgits to buttress the suture. This approach is readily executed via a large incision, but is more difficult through a keyhole incision or a thoracoscope.

The novel approaches according to still further embodiments of the present disclosure employ methods of applying traction that are much better suited to less invasive insertion. The following approaches offer significant advantages over suturing.

First, insertion of an expandable device into the chamber of the heart is accomplished through a small introducer sheath. The expandable device can be a specialized balloon catheter, a mechanical deployable 'umbrella', or a coil spring etc. The expandable device, once placed in the heart chamber, is deployed and traction applied to a tether or a catheter attached to the expanded device such that force is exerted against the interior wall of the heart chamber. In this fashion controlled traction is exerted on the wall of the heart chamber to gain control of the intended site for cannulation.

Alternatively, a traction device is applied to the wall of the heart using a vacuum. Such a device employs small suction cups connected to an external vacuum source. Once suction is achieved, traction is applied via suture tethers or mechanical rods, etc., to control the insertion site.

A fast curing tissue adhesive can be used to attach a circular ring, or the like, around the proposed insertion, and traction applied via suture tethers. The circular ring can be felt, polymeric material or any other suitable implantable material. Such a device may also be used to secure the position of the inflow cannula or pump within the cavity of the heart chamber.

The following steps are then taken to insert an inflow cannula or pump. Once the intended area of cannulation is immobilized and traction applied, the Seldinger technique is used to pass a wire guide into the heart chamber and, if desired, the guide wire can then be passed through a valve. Next, a progressive dilation system is used to enlarge the penetration at the access location sufficient to allow introduction of a thin walled sheath which would serve as the insertion conduit for an inflow cannula or pump.

The inflow cannula or pump is then passed through or around the insertion sheath into the heart chamber. The insertion sheath is designed to be removable (for instance, splittable like a banana peel) once the inflow cannula or pump is positioned in the heart chamber.

Then, the inflow cannula or pump is secured using a stabilizing device which either comprises a polymeric or elastomeric washer, or which employs a collar button shape. The stabilizer is optimized to capture the implanted cannula or pump and also has features that can be sutured, stapled or bonded to the chamber wall to secure the cannula or pump. The above method can be employed with the described devices, having a small pump and cannula and requiring only a small hole. The devices and methods of there insertion are so non-invasive, that in removal it should not be necessary to stop the heart in order to remove the LVAD support. The relatively small hole remaining won't take much to plug, and a small plug of suitable materials may be provided for placement in the hole after removal.

FIGS. 23A-F show a schematic step-wise representation of one particular minimally invasive delivery system and method that may be employed for transapical surgical implantation of a pump according to certain present embodiments, for purpose of further illustration of one particular overall system and method of use. More specifically, these figures show coordinated use of the following component devices in an overall delivery system: A thinwalled introducer 450 is placed through the heart wall 452 at the insertion site 454 into the heart chamber 456 (FIG. 23A). An expandable traction device 458 is placed through the introducer 450 into the heart chamber 456 and deployed to permit a traction force 460 to be applied to the insertion site 454 in the direction shown, thus stabilizing and controlling the heart wall 452 (FIG. 23B). A coring tool 462 with cutting edge 464 is pressed against the insertion site 454 (FIG. 23C) and rotated to incise a circular core of the heart wall 452 (FIG. 23D), producing an introduction opening 466 of sufficient size to permit insertion of the pump 468 into the heart chamber 456. The expandable traction device 458 tamponades the introduction opening 466 and thereby prevents blood from escaping from the heart chamber 456 during the coring operation (FIG. 23E). The pump 466 is then passed through the introduction opening 466 into the heart chamber 456 and secured to the heart wall 452 with standard surgical methods (FIG. 23F).

The following issued U.S. Patents are herein incorporated in their entirety by reference thereto: U.S. Pat. Nos. 4,625,712; 4,817,586; 4,846,152; 4,908,012; 4,944,722; 4,994,078; 5,049,134; 5,061,256; 5,092,879; 5,112,200; 5,211,546; 5,324,177; 5,370,509; 5,376,114; 5,695,471; 5,755,784; 5,776,190; 5,840,070; 5,888,241; 5,928,131; 5,947,892; 6,080,133; 6,227,797; 6,234,772; 6,234,998; 6,250,880; 6,293,901; 6,368,083; 6,530,876; 6,609,883; 6,638,011; 6,688,861; 6,866,625; and 6,966,748.

The following published US Patent Applications are herein incorporated in their entirety by reference thereto: US 2002/0102169; US 2004/0234397; US 2005/0084398; US 2005/0084399; US 2005/0095151; and US 2006/0030748.

The following article publications are herein incorporated in their entirety by reference thereto:

Dennis et al., "A left atrial cannulation without thoracotomy for total left heart bypass." Acta. Chir. Scand., 123: 276, 1962a.

Zwart, "Trans-arterial closed chest left ventricular bypass." Trans. Amer. Soc. Artif. Int. Organs, 15:386, 1969.

While this invention has been described in conjunction with the specific embodiments outlined above, it is evident that many alternatives, modifications and variations will be apparent to those skilled in the art. For example, whereas present embodiments may be described by reference to conductor wires connecting pump motors to external power sources, other power sources or energy coupling mechanisms may be used, such as integral batteries, implanted power sources. Such may further include, for example, implanted batteries that are either integral with the pump assembly or remotely implanted. In various locations, suitable batteries may furthermore have for example fixed charge life, or may be rechargeable, such as via motion actuation or via transcutaneous inductive coupling. According to another example, certain mating or cooperating parts such as rotor magnets and motor stator backirons are shown in specific relative locations to each other according to the specific illustrative embodiments. However, other specific arrangements relative between such components are also contemplated and may also be suitable or even of particular benefit in certain circumstances or applications. For example, whereas the back iron of motor stator embodiments shown is typically shown aligned with the rotor magnet, it may instead be partially longitudinally displaced from the rotor magnet in resting condition. This resting displacement may be configured in order to maximize the displacement force from the magnetic attraction between these components counter-directionally against opposite longitudinal displacement forces incurred by the rotor within the housing when the magnetic flux gap motor is activated.

Although the description above contains many details, these should not be construed as limiting the scope of the invention but as merely providing illustrations of some of the presently preferred embodiments of this invention. Therefore, it will be appreciated that the scope of the present invention fully encompasses other embodiments which may become obvious to those skilled in the art, and that the scope of the present invention is accordingly to be limited by nothing other than the appended claims, in which reference to an element in the singular is not intended to mean "one and only one" unless explicitly so stated, but rather "one or more." All structural, chemical, and functional equivalents to the elements of the above-described preferred embodiment that are known to those of ordinary skill in the art are expressly incorporated herein by reference and are intended to be encompassed by the present claims. Moreover, it is not necessary for a device or method to address each and every problem sought to be solved by the present invention, for it to be encompassed by the present claims. Furthermore, no element, component, or method step in the present disclosure is intended to be dedicated to the public regardless of whether the element, component, or method step is explicitly recited in the claims. No claim element herein is to be construed under the provisions of 35 U.S.C. 112, sixth paragraph, unless the element is expressly recited using the phrase "means for."

What is claimed is:

1. A heart assist device, comprising:
a rotary pump housing having a cylindrical bore, a pumping chamber at one end of the cylindrical bore and a motor stator including an electrically conductive coil located within said housing and surrounding a portion of said cylindrical bore, and also comprising a rotor, said rotor having a cylindrical shaft with an outer surface and at least one impeller appended to one end of said shaft;
wherein said rotor comprises a plurality of magnets located within said shaft and opposite said motor stator;
wherein said bore has an inner surface that is closely fitted to the outer surface of said shaft forming a journal bearing comprising a journal bearing clearance;
wherein when said rotor is positioned and rotates within said bore, said at least one impeller is positioned and rotates within the pumping chamber; and wherein said pumping chamber and said journal bearing are connected by a leak path to allow blood to pass between the pumping chamber and the journal bearing
wherein said rotor is solely suspended in the radial direction within said housing by hydrodynamic thrust forces generated by relative movement of said rotor with respect to and within said pump housing.

2. An implantable blood pump device, comprising:
a housing with an elongated cylindrical bore extending along a longitudinal axis, a pumping chamber, and a motor stator with an electrically conductive coil and back iron;
a rotor with an elongated shaft extending along a longitudinal axis, a rotary pump coupled to the elongated shaft, and a rotor magnet;
a blood inlet port fluidly coupled to the pumping chamber;
a blood outlet port fluidly coupled to the pumping chamber;
wherein the elongated shaft of the rotor is located at least in part within the cylindrical bore of the housing with a journal bearing clearance between an inner bearing surface of the housing's bore and an outer bearing surface of the rotor shaft;
wherein the rotary pump is located within the pumping chamber;
wherein the motor stator is adapted to be coupled to a power source and is positioned relative to the rotor magnet to form a flux gap motor interface such that, in an operating mode upon activation by the power source, electrical current flows through the coil sufficient to create a magnetic flux field that extends across a flux gap clearance between the rotor and housing at the flux gap motor interface and that displaces the rotor magnet sufficient to torque the rotor and rotate the rotor shaft and rotary pump within the journal bearing clearance and pumping chamber, respectively;
wherein in the operating mode blood flows into the pump principally along an inflow path inward through the inlet port and into the pumping chamber, and flows out from the pump principally along an outflow path outward from the pumping chamber through the outlet port;

wherein in the operating mode the back iron is positioned to provide a magnetic flux field interaction between the back iron and rotor magnet sufficient to substantially resist longitudinal displacement from a displacement force of the activated motor stator coil, and to substantially maintain a longitudinal position of the rotor within the housing; and wherein said pumping chamber and said journal bearing are connected by a leak path to allow blood to pass between the pumping chamber and the journal bearing clearance wherein said rotor is solely suspended in the radial direction within said housing by hydrodynamic thrust forces generated by relative movement of said rotor with respect to and within said pump housing.

3. The device of claim 1 or 2, wherein said shaft flares at an end longitudinally opposed to said impeller thereby forming a radial projection over at least a portion of said bore of said housing, said projection forming a hydrodynamic thrust bearing at the bore end portion for opposing axial thrusting of the rotor.

4. The device of claim 3, wherein the hydrodynamic thrust bearing comprises a booster pump that is adapted to enhance the leakage flow along the leak path.

5. The device of claim 1 or 2;

wherein the leak path extends along the journal bearing clearance to thereby form a hydrodynamic journal bearing.

6. The device of claim 5:

wherein the rotor shaft comprises a substantially solid or enclosed cylindrical shaft with a cylindrical outer surface that forms the journal bearing clearance with the bore of the housing; and wherein the leakage flow path extends along the journal bearing clearance between the rotor's outer surface and housing's interior bore surface.

7. The device of claim 1 or 2, wherein passage of blood into said pumping chamber is provided by inlets provided in said pump housing formed between said pumping chamber and said cylindrical bore.

8. A heart assist device, comprising:

a rotary pump housing having a cylindrical bore, a pumping chamber at one end of the cylindrical bore and a motor stator including an electrically conductive coil located within said housing and surrounding a portion of said cylindrical bore, and also comprising a rotor, said rotor having a cylindrical shaft with an outer surface and at least one impeller appended to one end of said shaft;

wherein said rotor comprises a plurality of magnets located within said shaft and opposite said motor stator;

wherein said bore has an inner surface that is closely fitted to the outer surface of said shaft forming a journal bearing clearance;

wherein when said rotor is positioned and rotates within said bore, said at least one impeller is positioned and rotates within the pumping chamber; and wherein said pumping chamber and said journal bearing are connected by a leak path to allow blood to pass from the pumping chamber into the journal bearing clearance while the rotor is rotating in said bore wherein said rotor is solely suspended in the radial direction within said housing by hydrodynamic thrust forces generated by relative movement of said rotor with respect to and within said pump housing.

9. The device of claim 8, wherein the leak path extends along the journal bearing clearance to thereby form a hydrodynamic journal bearing.

10. The device of claim 9, wherein the hydrodynamic thrust bearing comprises a booster pump that is adapted to enhance the leakage flow along the leak path.

11. The device of claim 8, wherein said shaft flares at an end longitudinally opposed to said impeller thereby forming a radial projection over at least a portion of said bore of said housing, said projection forming a hydrodynamic thrust bearing at the bore end portion for opposing axial thrusting of the rotor.

12. An implantable blood pump device, comprising:

a housing with an elongated cylindrical bore extending along a longitudinal axis, a pumping chamber, and a motor stator with an electrically conductive coil and back iron;

a rotor with an elongated shaft extending along a longitudinal axis, a rotary pump coupled to the elongated shaft, and a rotor magnet;

a blood inlet port fluidly coupled to the pumping chamber;

a blood outlet port fluidly coupled to the pumping chamber;

wherein the elongated shaft of the rotor is located at least in part within the cylindrical bore of the housing with a journal bearing clearance between an inner bearing surface of the housing's bore and an outer bearing surface of the rotor shaft;

wherein the rotary pump is located within the pumping chamber;

wherein the motor stator is adapted to be coupled to a power source and is positioned relative to the rotor magnet to form a flux gap motor interface such that, in an operating mode upon activation by the power source, electrical current flows through the coil sufficient to create a magnetic flux field that extends across a flux gap clearance between the rotor and housing at the flux gap motor interface and that displaces the rotor magnet sufficient to torque the rotor and rotate the rotor shaft and rotary pump within the journal bearing clearance and pumping chamber, respectively;

wherein in the operating mode blood flows into the pump principally along an inflow path inward through the inlet port and into the pumping chamber, and flows out from the pump principally along an outflow path outward from the pumping chamber through the outlet port;

wherein in the operating mode the back iron is positioned to provide a magnetic flux field interaction between the back iron and rotor magnet sufficient to substantially resist longitudinal displacement from a displacement force of the activated motor stator coil, and to substantially maintain a longitudinal position of the rotor within the housing;

wherein said journal bearing clearance is configured so that the rotor is solely supported by the journal bearing in the radial direction while the rotor rotates within said bore;

wherein said pumping chamber and said journal bearing clearance are connected by a leak path; and wherein in the operating mode a portion of the blood flows from the pumping chamber into the journal bearing clearance via the leak path.

13. The device of claim 12, wherein the leak path extends along the journal bearing clearance to thereby form a hydrodynamic journal bearing.

14. The device of claim 12, wherein said shaft flares at an end longitudinally opposed to said impeller thereby forming a radial projection over at least a portion of said bore of said housing, said projection forming a hydrodynamic thrust bearing at the bore end portion for opposing axial thrusting of the rotor.

15. The device of claim 12, wherein the hydrodynamic thrust bearing comprises a booster pump that is adapted to enhance the leakage flow along the leak path.

* * * * *